US005834195A

United States Patent [19]
Benkovic et al.

[11] Patent Number: 5,834,195
[45] Date of Patent: Nov. 10, 1998

[54] METHOD FOR IDENTIFYING MEMBERS OF COMBINATORIAL LIBRARIES

[75] Inventors: Stephen J. Benkovic, State College; Nicholas Winograd, Spring Mills, both of Pa.; Christopher L. Brummel, Newton, Mass.; Irene N. W. Lee, State College, Pa.

[73] Assignee: The Penn State Research Foundation, University Park, Pa.

[21] Appl. No.: 718,428

[22] PCT Filed: Mar. 23, 1995

[86] PCT No.: PCT/US95/03355

§ 371 Date: Dec. 18, 1996

§ 102(e) Date: Dec. 18, 1996

[87] PCT Pub. No.: WO95/25737

PCT Pub. Date: Sep. 28, 1995

Related U.S. Application Data

[63] Continuation-in-part of Ser. No. 217,046, Mar. 23, 1994, abandoned.

[51] Int. Cl.$^6$ .............................. G01N 33/53; C12Q 1/68
[52] U.S. Cl. ................................ 435/6; 435/7.1; 436/501; 436/518; 436/528; 436/531; 436/533; 436/173
[58] Field of Search ........................ 435/6, 7.1; 436/501, 436/518, 528, 531, 533, 173

[56] References Cited

U.S. PATENT DOCUMENTS 5,143,854 9/1992 Pirrung et al. ........................... 436/518

OTHER PUBLICATIONS

Benninghoven et al., "Detection, Identification and Structural Investigation of Biologically Important Compounds By Secondary Ion Mass Spectrometry", *Analytical Chemistry*, 50(8):1180–1184 (1978).
Benninghover et al., "Surface MS: Probing Real–World Samples", *Analytical Chemistry*, 65(14):630A–639A (1993).
Biemann et al., "Mass Spectrometric Determination Of The Amino Acid Sequence Of Peptides And Proteins", *Mass Spectrometry Reviews*, 6:1–76 (1987).
Brenner et al., "Encoded Combinatorial Chemistry", *Proc. Natl. Acad. Sci. USA*, 89:5381–5383 (1992).
Briggs et al., "Analysis of Polymer Surfaces By SIMS: 1. An Investigation Of Practical Problems*", *Surface And Interface Analysis*, 4(3):109–115 (1982).
Bunin et al., "A General And Expedient Method For The Solid–Phase Synthesis of 1, 4–Benzodiazepine Derivatives", *J. Am. Chem. Soc.*, 114:10997–10998 (1992).
Chait et al., "Time–Of–Flight Mass Spectrometer For Measurement of Secondary Ion Mass Spectra", *International Journal Of Mass Spectrometry And Ion Physics*, 40:185–193 (1981).
Cotter, "Time–Of–Flight Mass Spectrometry: An Increasing Role In The Life Sciences", *Biomedical And Environmental Mass Spectrometry*, 18:513–532 (1989).

Fodor et al., "Light–Directed, Spatially Addressable Parallel Chemical Synthesis", *Science*, 251: 767–773 (1991).
Gardella et al., "Static Secondary Ion Mass Spectrometry Of Polymer Systems", *Analytical Chemistry*, 52:226–232 (1980).
Houghten et al., "Generation And Use Of Synthetic Peptide Combinatorial Libraries For Basic Research And Drug Discovery", *Nature*, 354:84–86 (1991).
Jung et al., "Multiple Peptide Synthesis Method And Their Applications", *Angewandte Chemie International Edition in English*, 31(4):367–383 (1992).
Kerr et al., "Encoded Combinatorial Peptide Libraries Containing Non–Natural Amino Acids", *J. Am. Chem. Soc.*, 115:2529–2531 (1993).
Lam et al., "A New Type Of Synthetic Peptide Library For Identifying Ligand–Binding Activity", *Nature*, 354:82–83 (1991).
Leggett et al., "Surface Studies By Static Secondary Ion Mass Spectrometry: Cluster Ion Formation Studied By Tandem Mass–Spectro–Metric Techniques", *J. Chem. Soc. Faraday Trans.*, 88(3):297–309 (1992).
Mantus et al., "Static Secondary Ion Mass Spectrometry Of Absorbed Proteins", *Analytical Chemistry*, 65(10):1431–1438 (1993).
Mergler et al., "Peptide Synthesis By A Combination Of Solid–Phase and Solution Methods I: A New Very Acid–Labile Anchor Group For The Solid Phase Synthesis Of Fully Protected Fragments", *Tetrahedron Letters*, 29(32):4005–4008 (1988).
Mergler et al., "Peptide Synthesis By A Combination of Solid–Phase And Solution Methods II: Synthesis Of Fully Protected Peptide Fragments On 2–Methoxy–4–Alkoxy–Benzyl Alcohol Resin", *Tetrahedron Letters*, 29(32):4009–4012 (1988).
Poppe–Schriemer et al., "Sequencing An 'Unknown' Peptide By Time–Of–Flight Secondary Ion Mass Spectrometry", *International Journal of Mass Spectrometry And Ion Processes*, 111:301–315 (1991).
Steffens et al., "A Time–Of–Flight Mass Spectrometer For Static SIMS Applications", *J. Vac. Sci. Technol. A*, 3(3):1322–1325 (1985).
Winograd et al., "Prospects For Submicron Molecular Imaging With Ion Beams And Lasers", *Inst. Phys. Conf. Ser.*, 128(7):259–264 (1992).

(List continued on next page.)

*Primary Examiner*—Lora M. Green
*Attorney, Agent, or Firm*—Thomas J. Monahan

[57] ABSTRACT

A method to determine the molecular weights of femtomole or smaller quantities of small molecules, such as peptides, oligonucleotides, or heterocyclics, covalently attached to polystyrene beads on a grid, is presented using imaging time-of-flight secondary ion mass spectrometry (TOF-SIMS). The determination is made possible by selectively clipping the bond linking the small molecule to the bead, followed directly by a TOF-SIMS assay of the bead on the grid. The method can be applied to large numbers of polystyrene beads having different small molecules attached thereto for direct characterization of massive combinatorial libraries.

19 Claims, 13 Drawing Sheets

OTHER PUBLICATIONS

Winogard, "Ion Means And Laser Postionization for Molecule–Specific Imaging", *Analytical Chemistry*, 65:622A–629A (1993).

Weinstock et al., 1–(Carboxybenzyl)imidazole–5–acrylic Acids: Potent and Selective Angiotensin II Receptor Antagonists, *J. Med. Chem.*, 34:1514–1517 (1991).

Kennan et al., Potent Nonpeptide Angiotensin II Receptor Antagonists. 2.[1] 1–(Carboxybenzyl)imidazole–5–acrylic Acids, *J. Med. Chem.*, 36:1880–1892 (1993).

Della–Negra et al., New Method for Metastable Ion Studies with a Time of Flight Mass Spectrometer. Future Applications to Molecular Structure Determinations, *Analytical Chemistry*, 57:2035–2040 (1985).

Tang et al., Daughter Ion Mass Spectra from Cationized Molecules of Small Oligopeptides in a Reflecting Time–of–Flight Mass Spectrometer, *Analytical Chemistry*, 60:1791–1799 (1988).

Spengler et al., Fundamental Aspects of Postsource Decay in Matrix–Assisted Laser Desorption Mass Spectrometry. 1. Residual Gas Effects, *J. Phys. Chem.*, 96:9678–9684 (1992).

Kaufman et al., Sequencing of peptides in a time–of–flight mass spectrometer: evaluation of postsource decay following matrix–assisted laser desorption ionisation (MALDI), *J. Mass Spectrum*, 131:355–385 (1994).

Stevanovic et al., *Bioarganic & Medicinal Chemistry Letters*, 3(3):431–436 (1993) see p. 434.

Bray et al., Gas Phase Cleavage of Peptides from a Solid Support with Ammonia Vapour. Application in Simultaneous Multiple Peptide Synthesis., *Tetrahedron Letters*, 32(43):6163–6166 (1991) see Abstract.

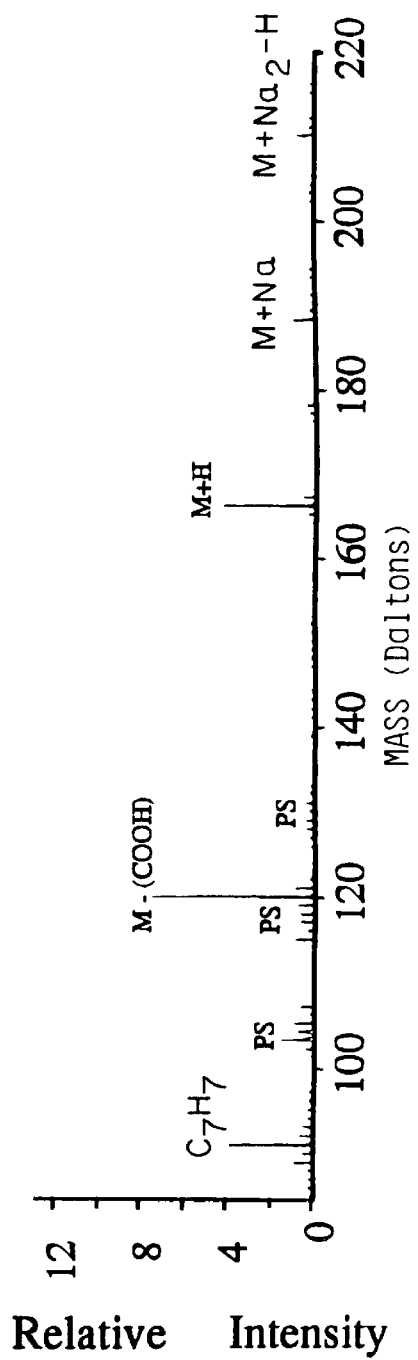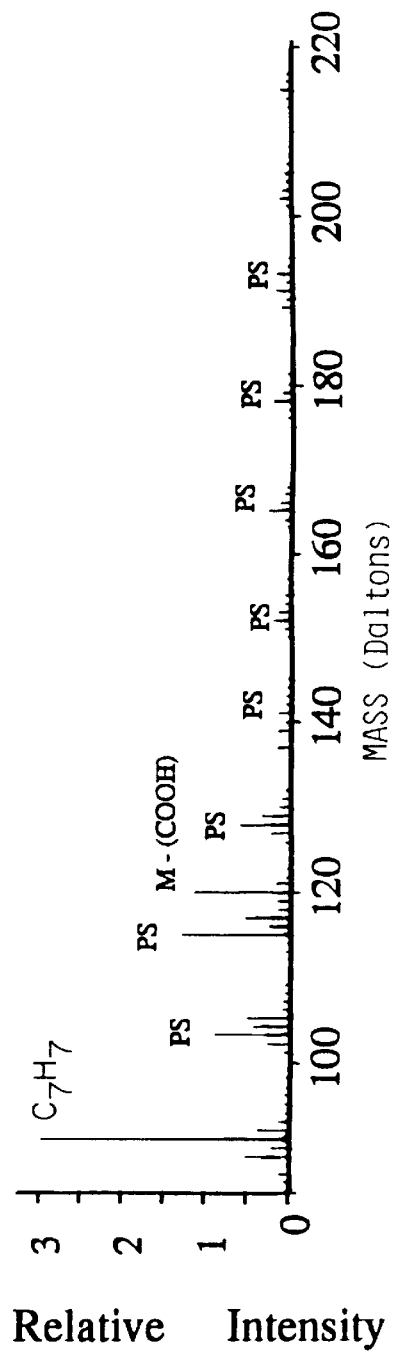

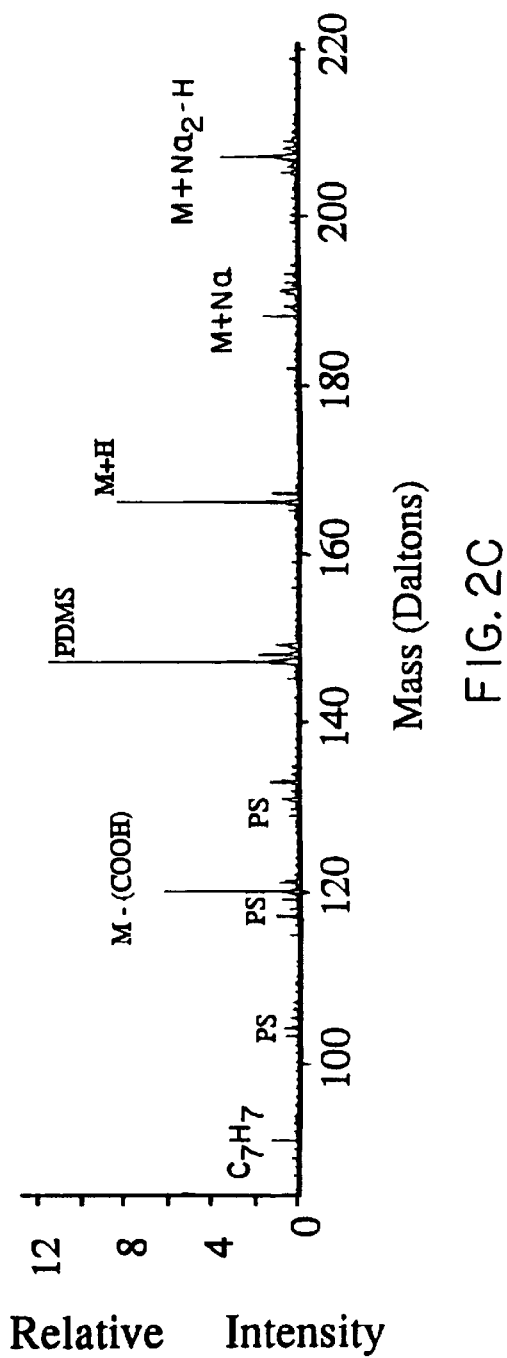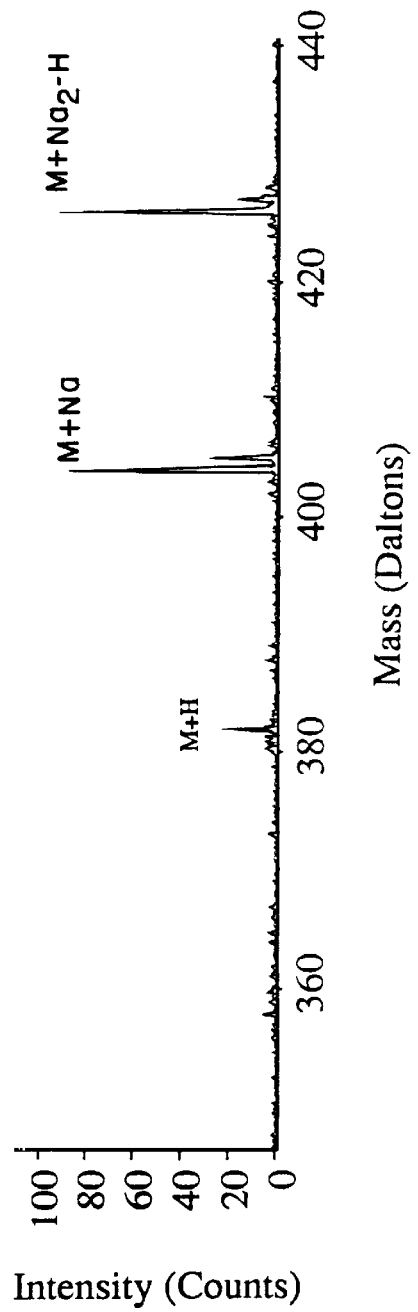

Distribution of phenylalanine

Distribution of Cu

Distribution of Leu

Distribution of Phe

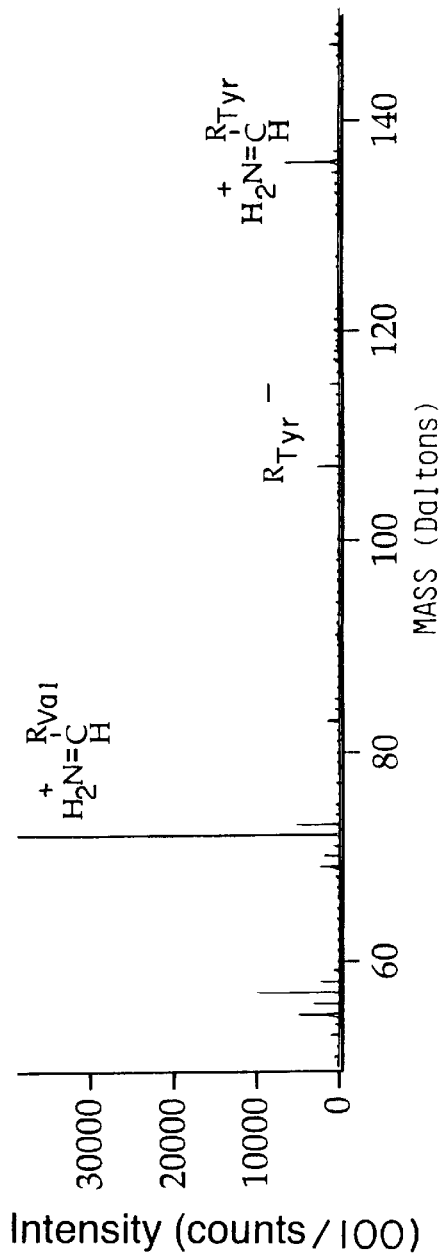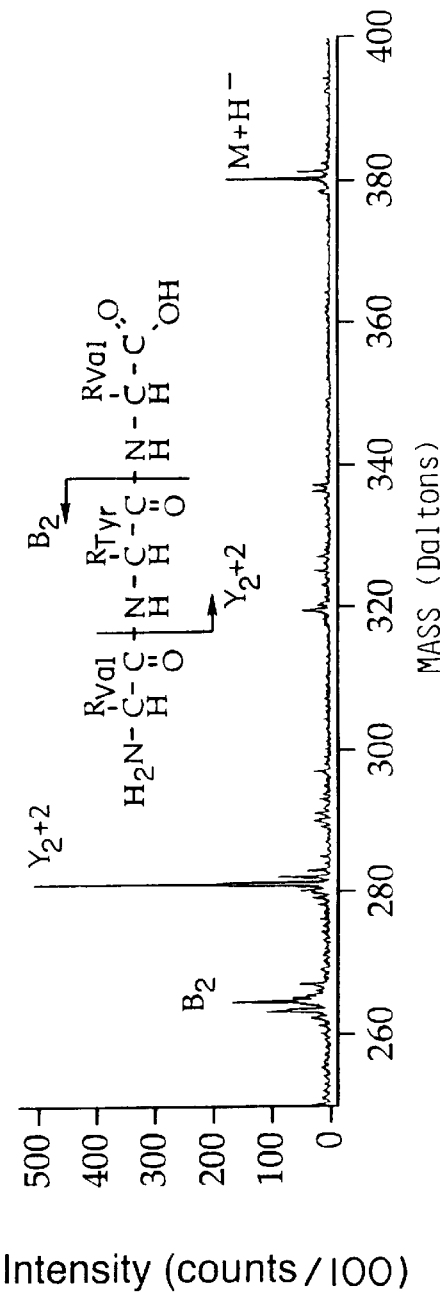
FIG. 6A
FIG. 6B

ANGIOTENSIN ANTAGONIST ON RESINS WITH DIFFERING ACID LABILITY

WANG RESIN-ACID LABILE, SB 218303

NITRO MERRIFIELD RESIN - PHOTO LABILE, SB 220126

THIOACETAL RESIN - ACID LABILE, SB 220127

ANGIOTENSIN ANTAGONIST ON RESINS WITH DIFFERING ACID LABILITY

ACETAL RESIN - ACID LABILE, SB 220128

SASRIN RESIN, SUPER ACID LABILE, SB 220261

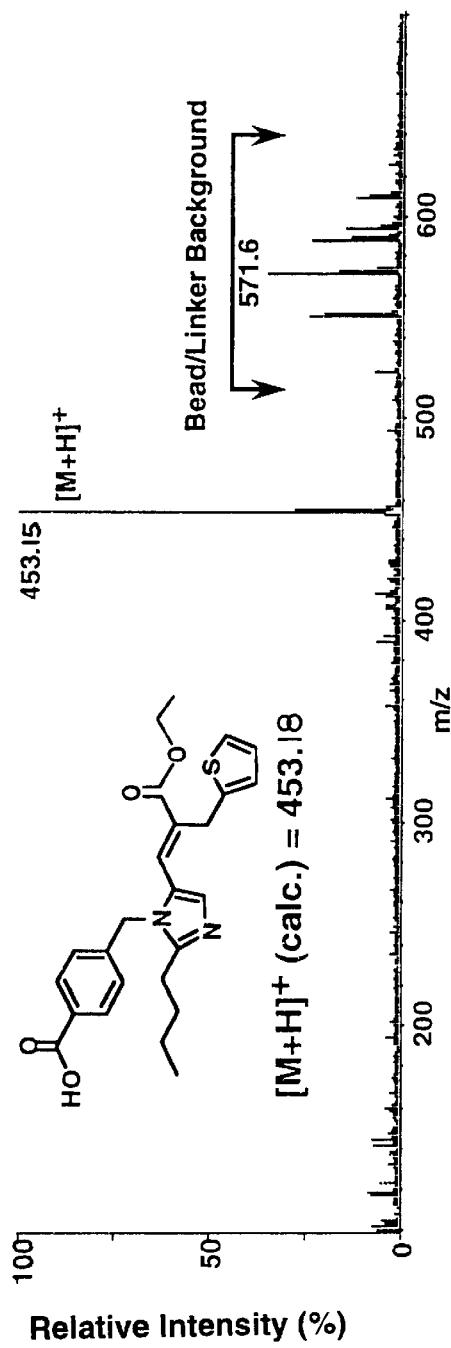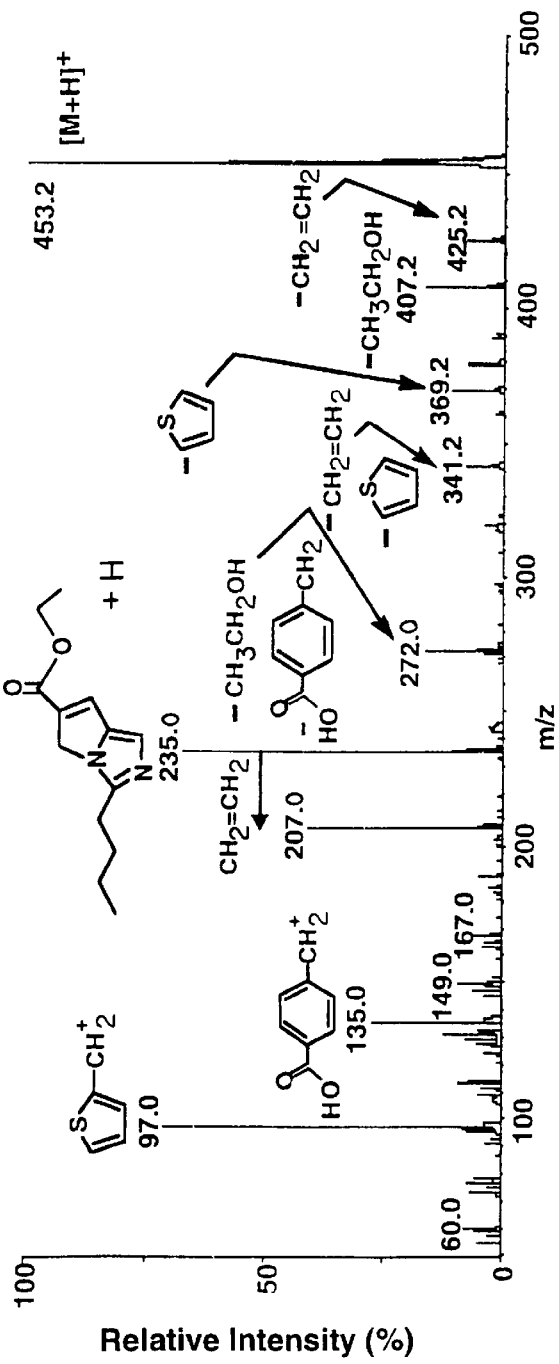
FIG. 8A
FIG. 8B

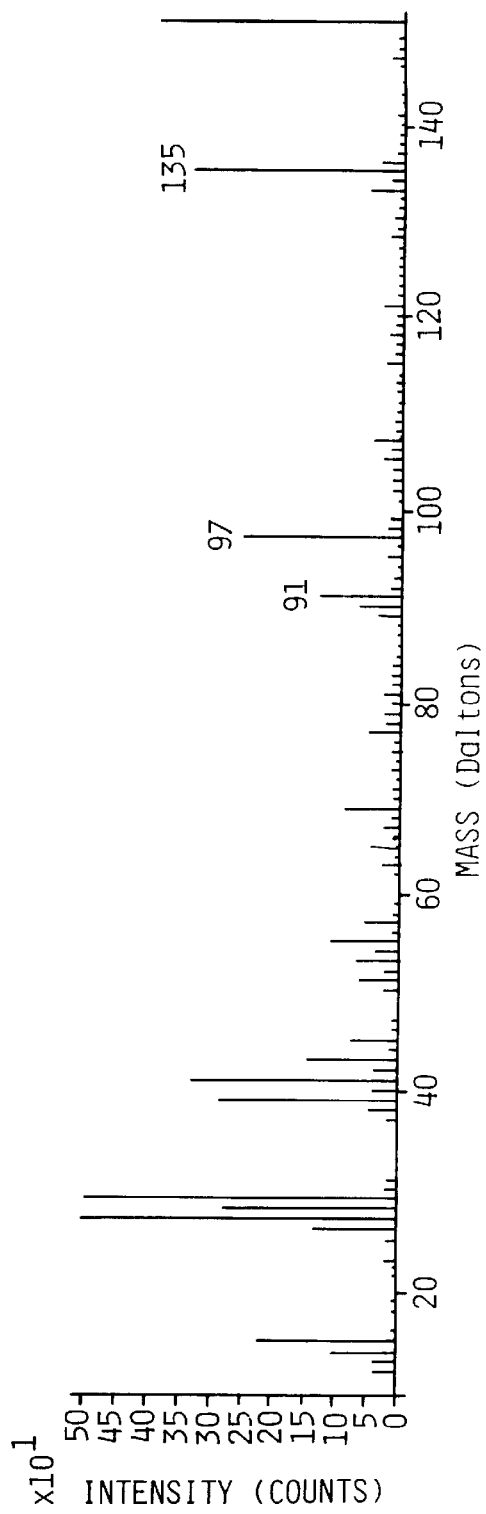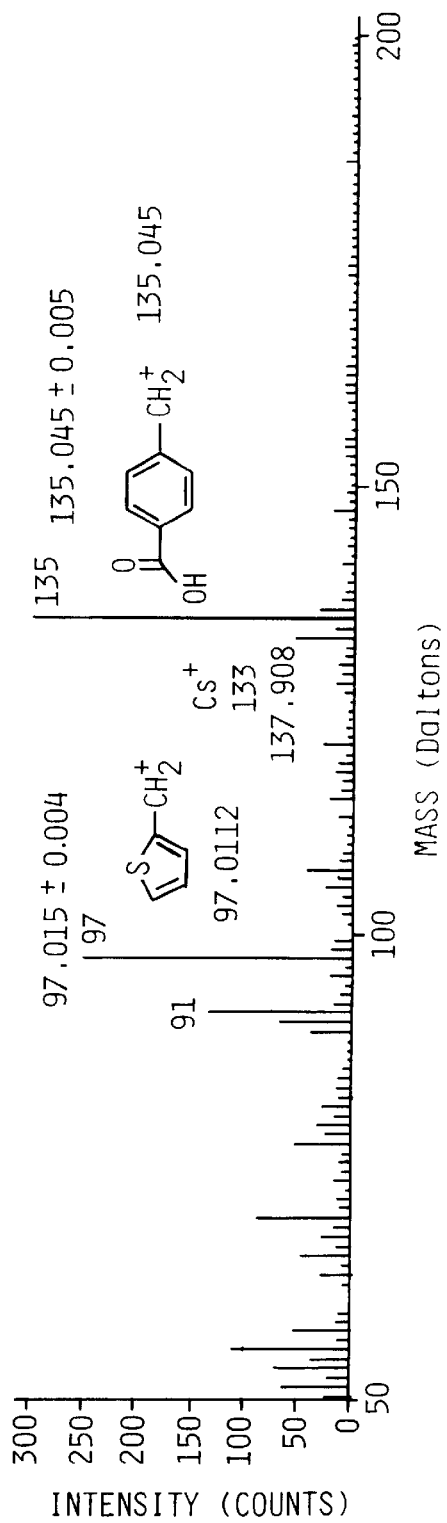

METHOD FOR IDENTIFYING MEMBERS OF COMBINATORIAL LIBRARIES

CROSS-REFERENCE TO RELATED APPLICATION

This is a continuation-in-part application of copending U.S. patent application Ser. No. 08/217,046, filed Mar. 23, 1994, now abandoned.

FIELD OF THE INVENTION

The present invention relates to a method for the identification and analysis of members of combinatorial libraries, wherein the identified member has a demonstrated pharmacological or physiological activity.

BACKGROUND OF THE INVENTION

Over the past ten years, there has been a growing demand for the production and identification of small molecules that have pharmacological activity as, for example, agonists or antagonists of various cellular acceptor molecules, such as cell-surface receptors, enzymes, or antibodies. Such small molecules can be peptides, oligonucleotides, or other organic compounds, such as heterocyclics and the like. The unifying feature of these small molecules is operational in that they bind specifically to known acceptors. In consequence of such binding, a physiological response occurs whereby certain biological processes are modulated, which can have applications in medicine and agriculture.

Searching for small molecules that are useful as pharmaceuticals entails (1) generating collections of such molecules, (2) screening such molecules for physiological activity, and (3) identifying the structure of molecules that provide a positive result in the screen. The first two steps can be accomplished using methods well-known in the art, some of which are described herein for purposes of clarity. The third step, where one determines the structure of a positively screened small molecule, has proven to be the time-limiting step in the overall process to discover new small molecule pharmaceuticals. This step is necessary to eliminate false positives or duplicates, and, of most importance, to produce the selected small molecule for a prospective pharmaceutical formulation.

Searching for such small molecules has involved screening collections of natural materials, such as fermentation products, plant or animal tissue extracts, or libraries of synthesized molecules. Chemical assays have been designed that merely identify those species that bind a particular acceptor molecule or, in a bioassay, assess the ability of tested molecules to effect certain physiological reactions. Screening of such collections often, at most, provides leads that must be refined by more stringent techniques and expanded testing of related molecules. All of these techniques are limited severely by the available concentration of any particular small molecule and the resolving power of the screening and analysis techniques. As a result, the process of production and identification of small molecules that have pharmacological activity, a process termed "irrational drug design" by Brenner and Lerner (*Proc. Natl. Acad. Sci. USA,* 89, 5381–5383 (1992)), "requires continual improvement both in the generation of repertoires [of small molecules] and in the methods of selection." Id. at page 5381.

A repertoire of small molecules, wherein each molecule thereof can be represented preferably in at least femtomole quantities, typically is produced by what are termed multiple methods of synthesis or parallel chemical synthetic protocols. Such repertoires are commonly referred to as "combinatorial libraries," for reasons that will become plain below.

With reference to peptides, such synthetic methods have been disclosed by Jung and Beck-Sickinger (*Angew. Chem. Int. Ed. Engl.,* 31, 367–383 (1992)). Methods for the production of heterocyclic libraries (see Bunin and Ellman, *J. Am. Chem. Soc.,* 114, 10997–10998 (1992)) and nucleic acid libraries (referred to in Brenner and Lerner, supra) have also been published. Other methods for the construction of combinatorial libraries include those of Kerr et al., *J. Am. Chem. Soc.,* 115, 2529 (1993); Lam et al., *Nature,* 354, 82 (1991); Houghten et al., *Nature,* 354, 84 (1991); and Fodor et al., *Science,* 251, 767–773 (1991) (see, also U.S. Pat. No. 5,143,854 (1992)).

In the methods cited above, members of a library are constructed from the coupling of chemical building blocks, such as amino acids, nucleic acids, or variant organic monomers and side groups. Resultant libraries consist of different individual species, the potential number (k) of which can be calculated as a function of the number of different building blocks used (a) and the number of different building blocks coupled to each member of the library (b), according to the following formula: $k=a^b$. Thus, a library of pentapeptides constructed using 20 different amino acids (i.e., the chemical building blocks) could include as many as $20^5$ or 3.2 million different species.

The method of Lam et al., supra, is presented as an example of one such method that provides a means to at least approach the theoretical maximum number of different species in a combinatorial library. The Lam et al. method employs a "split synthesis" protocol, in which standard solid phase peptide synthesis (see. e.g., Atherton and Sheppard, *Solid Phase Peptide Synthesis, A Practical Approach* (Oxford University Press, 1989)) is conducted on resin beads. Separate reactions for each amino acid used take place to couple covalently one amino acid to an aliquot of resin beads. For example, 20 different reaction vessels may be used, in which the resin beads are coupled to one of the 20 naturally occurring proteinogenic amino acids. Typically, the amino acids used in such reactions have been modified using suitable blocking groups known in the art to allow the coupling of only one amino acid per bead. After a first reaction, the aliquots of resin beads having attached thereto different single amino acids are combined, thus completing the first round. A second round to create dipeptides begins by removing the blocking group from the last amino acid added, re-allocating aliquots of the resin beads into another 20 reaction vessels, and allowing thereby the coupling of a second single amino acid to each resin bead. The combining of the resin beads having dipeptides completes round two. The rounds are repeated until the library of peptides has attained the desired number of building blocks, which, in this case, are amino acids.

According to the Lam et al. reference, each resin bead processed as recited above contained about 50 to 200 picomoles of peptide, which presumably each consisted of five amino acids. The library can then be screened for those beads that include peptides that are recognized by a particular acceptor molecule that is labelled directly or indirectly with fluorescein or an enzyme, for example, using materials and methods that are well known in the art. Such a labelled bead may be isolated physically using micromanipulation techniques, or its location, i.e., address, may be noted for further analysis in situ, i.e., in the midst of the nonselected, unlabelled beads of the library. An alternate approach, proposed by Brenner and Lerner, supra, would include an "appended 'genetic' tag" that would be interpreted to provide the structure of each molecular species in a library; however, this approach requires that the genetic tag be added chemically to the individual molecular species, which could interfere with the ability of a molecular species to interact with the acceptor molecule of interest. Even if the genetic tag presented no such obstacle, such tagged molecular species also would have to be "read" in the midst of multiples of the non-selected species. The current methods, in essence, have not overcome adequately the challenge presented in either isolating a labelled microscopic bead in view of the large numbers that require analysis (discussed further below) or in readily analyzing the identity of a molecular species attached to a labelled bead when surrounded by identical, unlabelled beads having different molecular species attached to them.

Presuming that the bead of interest can be isolated physically, the contained peptide may be analyzed for its sequence of amino acids using a commercially available peptide microsequencer, such as Model 477A of Applied Biosystems, for example. According to Lam et al., although "[a] library containing several million beads could be screened [with labelled acceptor molecules] in 10–15 Petri dishes in an afternoon[, only about] . . . three pentapeptide beads were sequenced daily using the microsequencer." Evidently, as understood from the technical literature presented hereinabove, the limiting step in the process of identifying new drugs from combinatorial libraries is the step of discarding false positives and determining the identity of the species of interest, which difficulty includes the step of either isolating the labelled bead(s) from unlabelled beads or having a sufficiently discerning technology available that can analyze the molecular species on a microscopic bead when adjacent to identical beads having different molecular species attached thereto.

In the instance of identifying a peptide of interest, for example, the time limiting step of extracting the sequence of those binding peptides, however, is also limitative in that only peptides containing naturally occurring amino acids can be identified. This limitation is due to characteristics of the Edman degradation technology upon which microsequencers are based. In addition to having the capability to sequence only a few peptides per day, microsequencers can only sequence peptides that include naturally-occurring proteinogenic amino acids.

Accordingly, the analysis of any combinatorial library is necessarily impeded by the very low rate at which, in the Lam et al.-type method, beads having members of the library attached thereto can be analyzed for the identity of the attached molecule. In view of the literally millions of candidate molecules to be screened in a given library, it is probable that at least hundreds, if not thousands, of the molecular species-attached beads would generate positive signals (including false positive signals) requiring further analysis. The limitation of being able to sequence only a few molecules per day, therefore, presents a strong drawback to current strategies of screening combinatorial libraries for pharmaceutical compounds. Moreover, if a method allowed analysis of a positively signalled bead having a small molecule of interest attached thereto without having to remove such a bead from the group of other beads, in the presence of which the bead was screened, the procedure of screening and identifying small molecules of interest would be greatly improved.

SUMMARY OF THE INVENTION

It has now been discovered that a direct mass spectrometric assay can be configured to read a wide variety of combinatorial libraries including those composed of peptides, oligonucleotides, and heterocyclic molecules. Using the present invention, any combinatorial library can be constructed on a suitable substrate and screened, and the individual substrate that is identified as having a molecule that specifically interacts with an acceptor molecule of interest (i.e., positive screen result) can be identified in the presence of identical substrates having other unselected molecular species attached thereto and subjected to direct mass spectrometric assay without removal from the total library to determine the precise molecular weight of the selected molecule. A preferred aspect of the method includes the use of novel linking moieties or substrates having reactive groups attached thereto that covalently or ionically link the individual molecules of the combinatorial library to the substrate, whereby the linkage may be broken without disturbing the molecule's structure, yet allow the library molecules to remain in close association with the substrate based on physical effects. Consequently, the present invention greatly improves the ability of artisans of the relevant art to identify pharmaceutically active agents derived from combinatorial libraries.

Accordingly, the present invention relates to a method of identifying individual small molecules of a combinatorial library comprising (a) forming a plurality of complexes of solid substrates and the small molecules, each of which comprises one substrate, or portion thereof, and one of the small molecules of said library; and (b) determining the molecular weight of a selected small molecules by means of secondary ion mass spectrometry. Suitable linking moieties and substrates having suitable reactive groups attached thereto that connect the small molecules to the substrate are disclosed as well.

These and other features and advantages of the invention will be more readily apparent upon reading the following detailed description of the invention and upon reference to the accompanying drawings, all of which are given by way of illustration only, and are not limitative of the present invention.

BRIEF DESCRIPTION OF THE DRAWINGS

FIGS. 2(A)–2(C) are a composite of three related mass spectrum profiles of phenylalanine attached to a polystyrene bead by various means, as follows: by physical adsorption (FIG. 2A); by covalent bonding (FIG. 2B); and by physical adsorption after vapor phase clipping with trifluoroacetic acid (TFA) of linking covalent bond(s) (FIG. 2C).

FIG. 3 is a profile of a tripeptide associated with a polystyrene bead by physical adsorption only and placed on a copper grid.

FIGS. 4A and 4B display the $(M+H)^+$ ion intensity for phenylalanine and copper, respectively.

FIGS. 5A and 5B display the $(M+H)^+$ ion intensity for leucine and phenylalanine, respectively.

FIGS. 6(A) and 6(B) are a profile of a tripeptide that was covalently linked to a polystyrene bead using an acid vapor labile linkage and then exposed to acid vapor, and then placed on a copper grid. Included with FIG. 6 is a representation of the structure of the tripeptide V-Y-V marked to indicate the fragments identified in the TOF-SIMS profile.

FIGS. 8(A) and 8(B) are the composite of two electrospray mass spectra of the angiotensin II receptor antagonist. This data was provided for comparison with the present invention by S. A. Carr, M. E. Hemling, G. D. Roberts, and J. Weinstock of the Chemical and Biological Research Division of SmithKline Beecham Pharmaceuticals, King of Prussia, Pa. FIG. 8A displays the standard electrospray mass spectrum and FIG. 8B displays the electrospray MS/MS spectrum.

FIG. 9A displays the standard MALDI spectrum and FIG. 9B displays the post source decay spectrum.

FIGS. 10(A)–10(D) are the TOF-SIMS mass spectrum of angiotensin II receptor antagonist on a Sasrin bead after cleavage by TFA/CH$_2$Cl$_2$ vapors.

FIG. 11A displays the image of the (M+H)$^+$ ion (m/z 453.2) and FIG. 11B displays the image of the fragment ion (m/z 135).

DETAILED DESCRIPTION OF THE PREFERRED EMBODIMENTS

Figure 1:
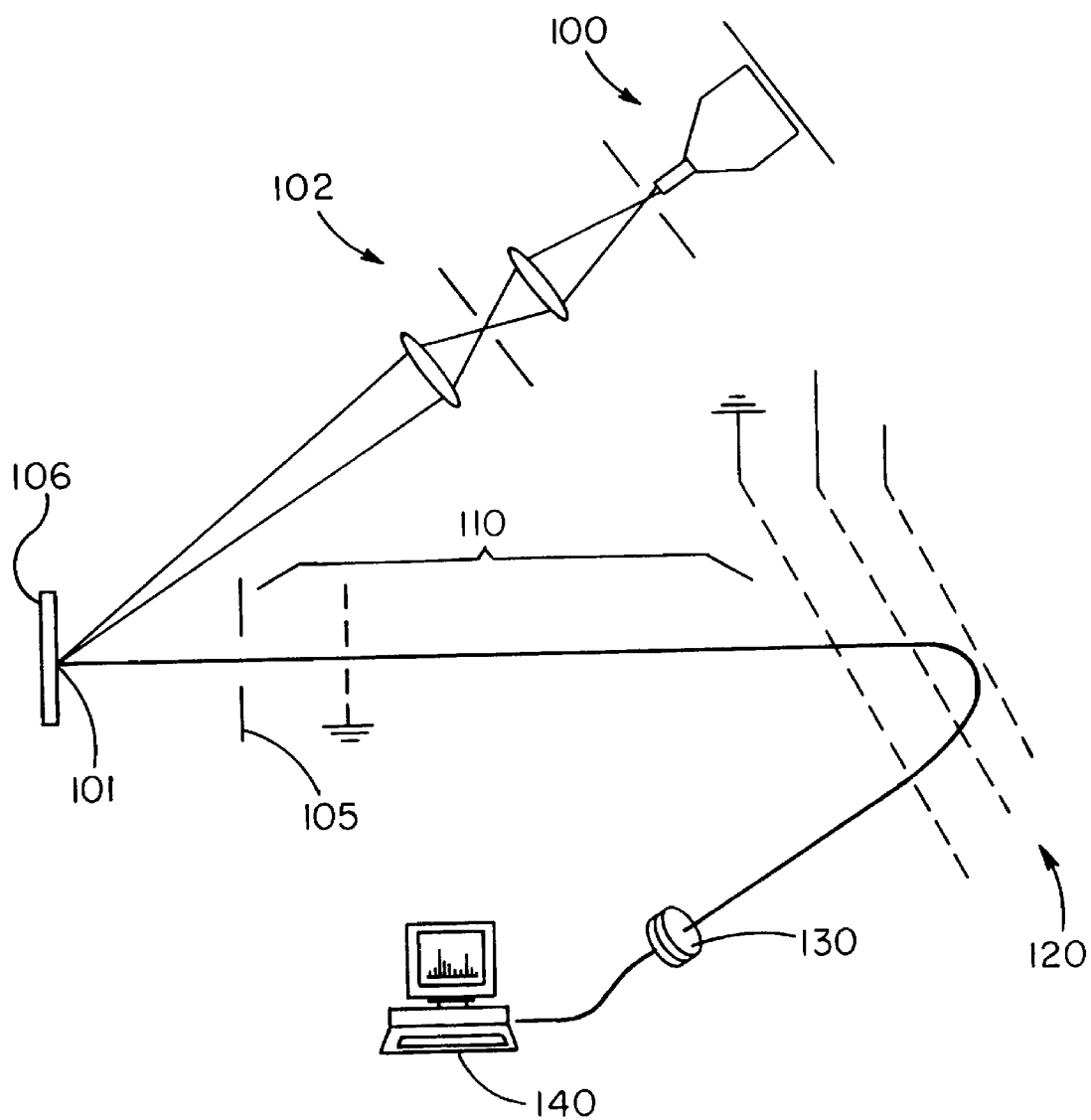
FIG. 1 is a schematic diagram of the imaging time-of-flight secondary ion mass spectrometry (TOF-SIMS) apparatus.

The following detailed description of the preferred embodiments of the instant invention is provided to aid those skilled in the art in practicing the present invention, but should not be construed to limit the present invention, as modifications and variations in the embodiments herein discussed may be made by those of ordinary skill in the art without departing from the spirit or scope of the present inventive discovery.

The present invention provides a method and novel materials used in the inventive method that greatly improves the ability of an ordinary artisan to identify and characterize pharmaceutically-active small molecules selected from a combinatorial library. The members of such a library preferably are constructed in association with a suitable substrate, such as a polystyrene bead surface. Such association between the small molecules and the substrates may be mediated by any suitable means, including, but not limited to, physical adsorption, covalent linkage, ionic bond, hydrophobic interactions, and van der Waals forces. Preferably, such associations are mediated by covalent or ionic linkage during the construction of such combinatorial libraries, wherein such a covalent or ionic linkage may be broken using means that does not modify or substantially modify the structure of the linked small molecule, and wherein the small molecule remains in association with the substrate via physical adsorption or other effects, but will allow desorption in a secondary ion mass spectrometry (SIMS) apparatus. Construction of such a library was described above in the Background section, using the method of Lam et al. (supra), as an example. Screening of such a library was also described above in the Background section. The present invention relates to the identification of a positively screened small molecule derived from the aforementioned combinatorial library.

A preferred identification approach would take into account the fact that small molecules, such as peptides, oligonucleotides, or heterocyclic compounds, may be constructed such that they can be desorbed intact or substantially intact from a substrate, particularly from a bead surface. Because each bead, for example, may have adsorbed thereto only a femtomole quantity of a particular molecular species, or less, extreme sensitivity of the method of analysis is required. For example, a standard 40 micron sphere covered with one layer of phenylalanine will only have about 50 femtomoles of surface molecules available for sampling.

The present method directly assesses the molecular weight of such molecular species upon their removal from the substrate and immediate subsequent ionization. The method employs imaging secondary ion mass spectrometry to identify the molecular weights of molecules adsorbed to the polystyrene bead surfaces, such as magnetic sector SIMS, quadrupole SIMS, Fourier Transformation SIMS, or time-of-flight SIMS (TOF-SIMS). The methodology actually used for any given SIMS analysis is known in the art, and may vary both with the machine used and artisan operating the machine. Preferably, the present invention employs TOF-SIMS. Detection of the mass of secondary ions formed in a TOF-SIMS protocol allows the unique identification of the corresponding library member, presuming that the method of construction of the library is known so that an artisan can assign discrete molecular weights to all molecular species and ionization fragments thereof (generated in the TOF-SIMS method).

In TOF-SIMS, a pulsed beam of primary ions is directed to a sample surface. The arriving primary ions desorb and ionize molecules of the sample present in a monolayer at the surface of the sample. These generated secondary ions are then accelerated to a uniform energy by an electric field, and drift through a fixed distance to a detector. The time-of-flight of these uniform energy particles through the fixed distance is directly proportional to the charge-to-mass ratio (m/z) of the ion. Because only the time-of-flight of an ion is measured to determine its mass, TOF-SIMS provides for parallel detection of all masses present in a sample, and an effectively unlimited mass detection range with high mass resolution. Indeed, TOF-SIMS provides a $10^4$–$10^6$ fold improvement in sensitivity over scanning mass spectrometric methods employing other detectors, such as magnetic sector fields and quadrapoles, which are well known in the art. TOF-SIMS thus provides a direct mass spectrometric assay that is generally applicable to reading a wide variety of molecular species assembled in combinatorial libraries.

The considerations relevant to use of TOF-SIMS for such assays are discussed in the literature. For example, as discussed by Winograd in *Ion Beams and Laser Postionization for Molecule-Specific Imaging* (*Anal. Chem.*, 65, 622A–629A (1993)), an energetic primary ion bombarding a sample on a solid surface creates a large amount of damage within 50 Angstroms of the point of impact. Unless the dose of incident ions is kept below approximately 1% of the number of sample molecules forming a monolayer, the ion bombardment alters the surface chemistry. The dose of incident ions of 1% is referred to as the "static limit." In TOF-SIMS, the dosage of primary ions remains below the static limit because the incident ion beam is directed toward the sample as a very short pulse. Use of a pulsed incident beam is also advantageous because a spectrum with a dynamic range of several orders of magnitude can be obtained by the accumulation of a large number of cycles with high repetition rates, as discussed by Benninghoven et al. in *Surface MS: Probing Real-World Samples* (*Anal. Chem.*, 65, 630A–639A (1993)). Increased sensitivity may also be realized using special cationization schemes or by laser postionization of sputtered neutral molecules, as discussed by Winograd et al., *Inst. Phys. Conf. Ser.*, 28, 259 (1992).

The TOF-SIMS technique also allows the primary ion beam to be focused to a spot size of less than 150 nm, thereby allowing the concentration of molecules to be mapped over small spatial domains by rastoring the ion beam across pixels defined on the sample and taking spectra at each pixel. Other aspects of TOF-SIMS imaging are discussed by Chait and Standing in *Time-of-Flight Mass Spectrometer for Measurement of Secondary Ion Mass Spectra* (*Int. J. Mass Spectrom. Ion Phys.*, 40, 185–193 (1981)); and by Steffens et al. in *A Time-of-Flight Mass Spectrometer for Static SIMS Applications* (*J. Vac. Sci. Technol.*, A 3(3), 1322 (1985)).

In certain situations, the information obtained by TOF-SIMS may not fully distinguish and identify all members of a combinatorial library. For example, various isomers of a given peptide may be present, each having the same mass, as, for example, in the case of phenylalanine-glycine-leucine and glycine-leucine-phenylalanine. In such situations, TOF-SIMS can be used to determine the sequence of the selected peptide nonetheless, provided that the library was constructed from a known set of building blocks. As discussed by Poppe-Schriemer et al. in *Sequencing an "Unknown" Peptide by Time-of-Flight Secondary Ion Mass Spectrometry* (*Int. J. Mass Spectrom. Ion Phys.*, 111, 301–315 (1991)), the parent ions subjected to TOF-SIMS necessarily break down to the various fragment ions, the masses of which can be compared and analyzed based on existing mass data to determine the structure of the selected peptide. This procedure is effective to the extent that the selected molecular species is one of the possible peptides of the combinatorial library as determined by the construction of the library. This procedure is also limited by the resolving power of TOF-SIMS to distinguish such fragmentions (TOF-SIMS mass accuracy is currently on the order of ±0.01 amu, according to Winograd, supra).

Alternatively, an isotope indexing scheme can be used to differentiate between molecular species that otherwise have the same mass. For example, to differentiate between phenylalanine-glycine-leucine and glycine-leucine-phenylalanine, one can either examine the fragmentation pattern in the SIMS spectrum or synthesize one of the peptides using leucine having $^{15}N$, an isotope that is readily distinguished in TOF-SIMS as its atomic mass is increased by one unit. Distinguishing between a leucine and an isoleucine residue, which are isomers, necessarily would require such an alternate method. Similarly, one could use differentially L and D amino acids, using methods well known in the art.

In particular, the present invention relates to a method of identifying small molecules of a combinatorial library comprising (a) forming a plurality of complexes of solid substrates and small molecules, each of which comprises one substrate, or portion thereof, and one of said small molecules of said library; and (b) determining the molecular weight of a selected small molecule by means of secondary ion mass spectrometry. Preferably, the secondary ion mass spectrometry that is utilized in the context of the present invention is TOF-SIMS, as noted above and exemplified below. The small molecules of such a combinatorial library are selected from at least one of the group consisting of amino acids, peptides, oligonucleotides, and heterocyclic compounds. The present inventive method is applicable to small molecules comprising amino acids that are naturally occurring or synthetic. A preferred combinatorial library has small molecules that are peptides or heterocyclic compounds; a more preferred combinatorial library has small molecules that are peptides.

Suitable peptides comprise as few as two amino acids to as many as about 30; preferably, suitable peptides comprise from about two amino acids to about fifteen; most preferably, suitable peptides comprise from about two amino acids to about ten. Any amino acid may be incorporated into peptides screened and identified using the present invention, including any combination of the naturally occurring proteinogenic amino acids as well as amino acids not naturally occurring in proteins such as, but not limited to, dextrorotatory forms of the known amino acids, for example.

Suitable oligonucleotides consist of as few as two nucleotides to as many as about 50; preferably, suitable oligonucleotides consist of from about five nucleotides to about 30; most preferably, suitable oligonucleotides consist of from about five oligonucleotides to about 15. Any nucleotide may be incorporated into an oligonucleotide screened and identified using the present invention, including any combination of the naturally occurring deoxyribonucleotides and ribonucleotides as well as those not naturally occurring in biological systems, such as, but not limited to, H-phosphonate derivatives, N-blocked-5'-O-DMT-deoxynucleoside 3'-(2-cyanoethyl-N,N-diisopropyl) phosphoramidites, N-blocked-5'-O-DMT-deoxynucleoside 3'-(2-cyanoethyl-N,N-diisopropyl)phosphoramidites, N-blocked-5'-O-DMT-deoxynucleoside 3'-(methyl-N,N-diisopropyl) phosphoramidites, N-blocked-5'-O-DMT-deoxynucleoside 3'-(2-chlorophenyl) phosphates, N-blocked-5'-O-DMT-deoxynucleoside 3'-(2-chlorophenyl 2-cyanoethyl) phosphate, all of which are nucleoside derivatives used in oligonucleotide synthesis.

Suitable heterocyclic compounds consist of, at minimum, a single four membered ring to as much as a multiple of four membered or greater membered rings coupled by carbon chains of 1 to about 20 atoms in length, such chains being saturated or not. Preferably, suitable heterocyclic compounds include a single four- to seven-membered ring, as well as, but not limited to varying combinations of 5, 6, or 7 membered rings having varying numbers of N, S, or O atoms. More preferably, suitable heterocyclic compounds include benzodiazepine and derivatives thereof (as, for example, disclosed in Bunin et al., *J. Am. Chem. Soc.*, 114, 10997–10998 (1992)), penicillins, cephalosporins, and folate derivatives. Most preferred, suitable heterocyclic compounds include benzodiazepine and derivatives thereof, and angiotensin II receptor antagonists. For example, one angiotensin II receptor antagonist that was developed to block the renin-angiotensin system for the treatment of heart failure and possibly chronic renal failure (see, Weinstock et al., *J. Med. Chem.*, 34, 1514 (1991); Keenan et al., *J. Med. Chem.*, 36, 1880 (1993)) can be identified in a mixture of other heterocyclic compounds using the present invention. The formula of the aforementioned angiotensin II receptor antagonist, ethyl 2-(2'-thiophenylmethyl)-3-[5'-{(1'-p-carboxyphenylmethyl)-2'-n-butyl}-imidazolyl]-propenoate, covalently linked to polystyrene beads through various linking moieties is set forth in FIG. 7. The present invention may be applied to the identification of derivatives of such compunds as benzodiazepine and the noted angiotensin II receptor antagonist.

Mixed libraries of small molecules comprising amino acids, peptides, oligonucleotides, and heterocyclic compounds may be prepared by following standard methods known to one of ordinary skill in the art. An oligonucleotide can be, for instance, linked to a peptide through the 5'-hydroxyl of the oligonucleotide. The peptide end can be modified to include a carboxyl group. A process of esterification of the carboxyl group with the 5'-hydroxyl of the oligonucleotide is used to produce a mixed library containing peptide-oligonucleotide species. Brenner et al., (*Proc. Nat'l Acad. Sci. USA,* 89, 5381–5383 (1992) also describes a method of preparation of mixed libraries having nucleotides and peptides. A mixed library comprising a heterocyclic compound and a peptide is also prepared by the reaction of suitable functional groups present on the heterocyclic compound. For instance, the carboxyl group on a heterocyclic compound is reacted with the amino group on the peptide to provide an amide linkage.

The small molecules of the combinatorial library preferably are linked covalently to the substrate, using methods well known in the art. A preferred covalent linkage between the small molecule and the substrate has the characteristic of being able to break in response to external changes at levels that do not modify substantially the structure of the small molecules of the combinatorial library. Such a covalent linkage may be effected, for example, by means of a suitable linking moiety that couples both to the small molecule and the substrate or a substrate having suitable reactive groups coupled thereto. In essence, a suitable covalent linkage will break conditionally. When a linking moiety or a substrate-bound reactive group is used, the covalent bonds between the small molecule and the substrate will break at one or more of its internal covalent bonds or a bond that it forms with either the substrate or the small molecule or both, thereby destroying any covalent linkage between the small molecule and the substrate. At least an appreciable proportion of the population of small molecules will be fully free of the covalent linkage, however, some or even a majority of the small molecules may remain attached covalently. The proportion of small molecules whose covalent linkage to the substrate are broken, however, may remain associated with the substrate by weaker molecular interactions, such as, but not limited to physical adsorption, hydrophobic interactions, and van der Waals forces. Suitable condition changes that may be used to effect the bond break or breaks of the covalent linkage include effective levels of temperature, electromagnetic radiation, sound or acidity at a level that leaves the small molecules of the library intact but still in association with the substrate via some combination of the aforementioned or other weak molecular interactions.

Suitable linking moieties are those that comprise a reactive functional group selected from the group consisting of alcohol, amino, carboxyl, acetal, thioacetal, and aminoalkyl, aralkyl, amino aralkyl, and haloalkyl, and a nitroaromatic group having a benzylic hydrogen ortho to the nitro group, such as o-nitrobenzyl derivatives, and benzylsulfonyl derivatives; and are cleavable by suitable vapor or photochemical means. Preferably, the linking moiety comprises at least one reactive group that is selected from the group consisting of hydroxyl, amino, carboxyl, acetal, thioacetal, $C_1$–$C_{10}$ alkylamino, $C_1$–$C_{10}$ aralkylamino, and $C_1$–$C_{10}$ haloalkyl, and an ortho-nitrobenzylic group having a benzylic hydrogen. Photoremovable groups are discussed in U.S. Pat. No. 5,143,854 to Pirrung et al., for example.

In particular, suitable linking moieties include p-alkoxybenzyl alcohol (used in the Wang resin), F-moc-2, 4-dimethoxy-4'-(carboxymethyloxy)-benzhydrylamine, F-moc-4-methoxy-4'-(gamma-carboxypropyloxy)-benzhydrylamine, 4-hydroxymethyl-phenoxy-acetic acid, aminomethyl (used in the PAM resin), benzhydrylamine, Cl—$CH_2$-Ph-(used in Merrifield resin), benzylacetal (used in the Acetal resin), benzylthioacetal (used in the Thioacetal resin), and 2-methoxy-4-alkoxybenzyl alcohol (used in Sasrin® resin). Preferred linking moieties include F-moc-2,4-dimethoxy-4'-(carboxymethyloxy)-benzhydrylamine, F-moc-methoxy-4'(gamma-carboxypropyloxy) benzhydrylamine, p-alkoxybenzyl alcohol, benzhydrylamine, Cl—$CH_2$-Ph, 2-methoxy-4-alkoxy benzyl alcohol, 6-nitroveratryloxy carbonyl, 2-nitrobenzyloxycarbonyl, and α,α-dimethyl-dimethoxybenzyloxycarbonyl, more preferred linking moieties include 2-methoxy-4-alkoxybenzyl alcohol. It is appreciated that different linker chemistry may enhance the molecular ion signal of covalently attached species.

The covalent linkage between the substrate and the small molecule may also be mediated by the reactive group or groups attached to the substrate. For example, as recited above, the polystyrene-derivative bead known as Sasrin® (Bachem Biosciences) has a reactive group (2-methoxy-4-alkoxy benzyl alcohol) that covalently couples to carboxylic acid groups found on all peptides. The covalent bond formed by the coupling of these two groups is acid labile. Accordingly, the exposure of TFA vapor to a small molecule covalently bound to a Sasrin® bead results in the breaking of certain covalent bonds associated with the Sasrin® bead, i.e., the linking moiety, thereby releasing an intact molecular species.

TFA is used preferably as a dilute solution in a suitable organic solvent. The concentration of TFA is preferably kept in the range of about 0.5% to about 2% by weight, and more preferably from about 0.75% to about 1.5%, and most preferably from about 0.9% to about 1.1% by weight of the solution. The TFA is applied in concert with a means for swelling the polystyrene beads, such as, for example, dissolving the TFA in an organic solvent. Preferred organic solvents include halogenated lower aliphatic hydrocarbons having 1–3 carbon atoms, including methylene chloride, chloroform, dichloroethane, 1,1,2,2-tetrachloroethane, trichloroethylene, tetrachloroethylene, and the like, with methylene chloride being more preferred.

The substrate upon or with which the small molecules of the combinatorial library are synthesized and/or associated may be any suitable substrate, including, but not limited to, resin, polystyrene, Sasrin®, Wang resin, Pam resin, and Merrifield resin, further including suitable combinations thereof. Such resins are commercially available from Bachem Bioscience Inc., for example. The substrate used in the present invention may be formed into any suitable shape, including, but not limited to, spheres, cubes, rectangular prisms, pyramids, cones, ovoids, sheets, and cylinders. Particularly when the substrate is used in the form of a sheet, such as when placed on the surface of a glass microscope slide, defined portions of the sheet may be apportioned for different small molecules of a combinatorial library, as disclosed in Fodor et al., supra. Preferably, the substrate as used in the present invention is formed into small particles that occupy no more than nine ten thousandths of a cubic millimeter, such as a sphere having a diameter of 120 microns, each of which has associated thereto a single small molecule structure. More preferred, the substrate used in the present invention is a bead or sphere having a diameter that is from about 10 microns to about 120 microns. Most preferred, the substrate used in the present invention is a bead or sphere having a diameter that is from about 20 microns to about 80 microns.

The present invention also relates to the linking moiety per se. The characteristics and examples of the linking moiety are the same as discussed above relative to the method for identifying individual small molecules.

The following examples further illustrate the present invention and, of course, should not be construed in any way as limiting its scope.

EXAMPLE 1

This example illustrates the use of TOF-SIMS for the identification of the molecular weights of combinatorial library constituent molecules bound to the polystyrene bead surfaces. TOF-SIMS is an instrument that is well known in the art and available from various commercial sources. Accordingly, an artisan may use any such TOF-SIMS in accordance with the specific machine's operating instructions. What follows is a description of the use of one TOF-SIMS instrument manufactured by Kratos, Inc. (Ramsey, N.J.), which was used in the context of the present invention.

A schematic diagram of the apparatus is shown in FIG. 1. An ion gun 100 is used to generate a beam of primary ions directed at a bead 101 coated with a monolayer of the sample. The ion gun 100 is illustrative of the liquid metal type (LMIG), and provides a source of $Ga^+$ ions having an energy of 25 keV. The dosage of these ions is limited to stay within the static limit by limiting sample exposure to 200,000 pulses of 500 pA current and 20 ns duration per pulse. This exposure corresponds to $10^7$ $Ga^+$ ions focused into a circular area of 40 μm diameter (the diameter of the bead) or $8\times10^{11}$ $Ga^+$ ions/cm$^2$. A 20 ns primary ion pulse yields a mass resolution of ~1500 at m/z 100. Pulsing of the beam is achieved by rapid electrical deflection of the beam through an aperture for the desired pulse duration. The ion beam is focused to a spot size of approximately 150 nm on the surface of the bead 101 through focusing optics denoted generally by reference numeral 102. Since a plurality of beads are held on a single copper grid, the ion gun beam may be rastored across the surface, with spectra being taken at each pixel to determine the surface constituents there.

Bombardment of a bead 101 by the ion beam causes the liberation of secondary ions from the surface. Secondary ions liberated from the surface of the bead 101 by the incident ion pulse are then accelerated to a uniform energy and are focused by an extraction lens 105. This lens is a combination of a flat extraction plate and an enzel lens. As will be discussed in greater detail below, a constant voltage is maintained between the copper grid 106 to which the bead is attached and the extraction lens 105. Preferably, the distance from the grid 106 to the extraction lens 105 is about 3 mm. Once through the extraction lens 105, the uniform energy ions travel along the linear path designated generally by reference numeral 110. Focusing optics, preferably in the form of a reflectron 120, are placed at the end of the path 110. These focusing optics correct for angular distribution of the secondary ions, as described in Cotter, *Biomed. Environ. Mass Spec.*, 18, 513–532 (1989). The focused secondary ions are then detected by a channelplate detector 130 located at the end of the TOF analyzer defined by path 110 and reflectron 120. Preferably, the length of the TOF analyzer is about 2 m. The channelplate detector 130 is connected to a computer 140, which performs processing required for spectrum analysis. Further electronics, not shown, are used for synchronizing the system so that the time between generation of secondary ions and their arrival at the channelplate detector 130 is accurately measured.

To accelerate the secondary ions to a uniform energy, a constant voltage is maintained between the substrate 106 and the extraction lens 105. This voltage is preferably 7200 volts, with the copper grid being held at +2.5 kV, and the extraction lens being held at −4.7 kV (for positively charged secondary ions). The polarity and magnitude of these signals may be changed to allow for detection of negatively charged species. Two mechanisms present in this configuration can lead to higher signals at the leading edge of a given bead. Because the ion current densities generated by the ion gun 100 are quite large, some charging of the sample occurs during bombardment. Further, because the bead has a physical dimension (illustratively a 40 micron diameter) in the 3 mm extraction gap, a voltage gradient on the order of 150 V across the bead may be present. The size of this gradient is affected by the size and shape of the bead and the angle of incidence of the $Ga^+$ ion. To compensate for charging of the bead, the sample may be flooded periodically with low energy electrons, such as 50 nA/cm$^2$ of 30 eV electrons for 50 μs between each $Ga^+$ ion pulse, to eliminate charging artifacts.

EXAMPLE 2

This example illustrates the TOF-SIMS spectrum of a 40 micron polystyrene bead coated with an approximately one molecular layer of phenylalanine.

Standard 40 micron diameter polystyrene beads (Bachem Bioscience) were treated with a solution of phenylalanine to cover the beads with a monolayer of the amino acid by physical adsorption, as follows: Polystyrene beads were immersed in a $10^{-4}$M methanol solution of phenylalanine, removed after several minutes, allowed to air dry, and then placed on a copper grid for analysis. For these measurements, the dose of incident 25 keV $Ga^+$ ions was controlled by limiting sample exposure to 200,000 pulses of 500 pA current and 20 ns duration per pulse. This exposure corresponds to $10^7$ $Ga^+$ ions focused into a circular area of 40 pm diameter or $8\times10^{11}$ $Ga^+$ ions/cm$^2$. A 20 ns primary ion pulse yields a mass resolution of ~1500 at m/z 100. The low dose of primary ions ensures that sample damage does not alter the chemical nature of the target surface, as noted by Benninghoven and Sichterman (*Anal. Chem.*, 50, 1180 (1978)).

As shown in FIG. 2A, the resultant TOF-SIMS spectrum exhibits large peaks at m/z 120 $(M-CO_2H)^+$, 166 $(M+H)^+$, 188 $(M+Na)^+$, and 210 $(M+H+Na_2)^+$. Other peaks characteristic of bulk polystyrene (labeled "PS" at m/z 91 ($C_7H_7$), 103, 105, 115, 117, 127, 128, 129, 141, 152, 165, 178, 190, and 193; see Leggett et al., *J. Chem. Soc. Faraday Trans.*, 88, 297 (1992)), sodium (at m/z 23), also assignable.

Although sensitivity of the TOF-SIMS technique varies depending on the molecular character of the sample being tested, it is noteworthy that for phenylalanine adsorbed on a polystyrene bead, the detection limit was approximately 500 attomoles on the bead surface.

Considering the capability of a 40 micron sphere to have adsorbed to it at least 50 femtomoles, i.e., at least 100 times above the detection limit, the TOF-SIMS technique was shown hereby to have the requisite sensitivity for analyzing combinatorial libraries according to the present invention.

Thus, this example illustrates the capability of TOF-SIMS to analyze small quantities of amino acids adsorbed on beads.

EXAMPLE 3

This example illustrates the TOF-SIMS spectrum of a 40 micron polystyrene bead coated with an approximately one molecular layer of the tripeptide, valine-tyrosine-valine (V-Y-V).

Standard 40 micron diameter polystyrene beads (Bachem Bioscience Inc.) were treated with a solution of V-Y-V to cover the beads with a monolayer of the tripeptide by physisorption and then placed on a copper grid, as described in Example 2. For the TOF-SIMS assay, the pulsed $Ga^+$ ion beam was rastored across the 100 micron field, during which time a TOF-SIMS spectrum was recorded (FIG. 3) for each ~1 square micron pixel. An image was rendered by mapping the intensity of $(M+H)$, $(M+Na)^+$, and $(M+H+Na_2)^+$ ions at m/z 380, 402 and 424, respectively. For V-Y-V, the intensity was generally 0–4 counts per pixel. In spite of these relatively low count rates, a clear image of the coated bead was discerned easily in a photograph of the noted intensity levels recorded and digitized in each pixel.

A number of points important in the interpretation of results derived from the inventive method can be made with reference to the V-Y-V analysis. First, although the copper grid is electrically conductive, the polystyrene bead itself is an electrical insulator subject to charging. Normally, in static TOF-SIMS experiments, charging is not a significant problem, due to the small number of incident ions needed to record a spectrum. For imaging of small areas, as done to generate the image just mentioned, however, ion current densities are much higher, therefore some type of charge compensation is essential. In the experiments accomplished in the course of elucidating the present invention, the sample was flooded with 50 $nA/cm^2$ of 30 eV electrons for 50 microseconds between each $Ga^+$ ion pulse to eliminate charging artifacts, after the methods disclosed in Gardella and Hercules (*Anal. Chem.*, 52, 226 (1980)) and Briggs and Wooton (*Surf. and Int. Anal.*, 4, 109 (1982)).

Second, the influence of the shape of the particle on which the molecular species of the library are attached and the angle of incidence of the $Ga^+$ ion stream have an impact on results. In the configuration used in the context of the present inventive method, the $Ga^+$ beam was incident at 45° from the surface normal to generate the data displayed in FIG. 3. For example, a polystyrene sphere of ~60 microns in diameter, placed in a 3 mm extraction gap, will have a field of 7200 volts applied across it. Accordingly, in addition to problems dictated by the morphology of the bead, there is a 150 volt field gradient across the bead. Both of these effects tend to produce higher signals near the leading edge of the bead, as is visualized in the digitized images shown in FIG. 4, for example.

Third, each of the TOF-SIMS assays reported herein was completed in less than 4 minutes. The analysis time is determined by the flux of incident ions and the time required to reach the damage threshold. For small beads and/or higher current sources, the analysis time could be reduced significantly by about an order of magnitude.

Similar results to those shown in FIG. 3 have been obtained using glycine-proline-glycine-glycine, as well as a variety of other small peptides. The technique for larger peptides, such as bradykinin, for example, having 11 amino acid residues, provided a recognizable TOF-SIMS spectrum when the 11-mer was adsorbed onto a polystyrene film (see Steffens et al., supra). Because combinatorial libraries of peptides on polystyrene beads generally consist of linear chains of only three to six amino acids, the range imaged by TOF-SIMS is certainly sufficient to determine the parent molecular ion of the adsorbed peptides of such libraries.

Accordingly, using the tripeptide V-Y-V, this example provides elucidation of important parameters in the direct imaging of a combinatorial library of peptides adsorbed onto polystyrene beads. One must be cognizant of the charging capacity of the substrate to which the molecular species of a library are adsorbed because of the substrates' capacity to increase the ion current density. Additionally, the shape of the substrate used and the angle of incidence of the $Ga^+$ ion can tend to produce artificially higher signals, and therefore must be compensated for using methods well known in the art. Finally, the time per TOF-SIMS was only four minutes, and could be reduced significantly, which is one of the surprising improvements that the present invention provides to the field of combinatorial library screening and analysis.

EXAMPLE 4

This example illustrates the determination of the molecular weight of a peptide at a particular address, using the TOF-SIMS assay as described in Example 2 and a novel method to reversibly yet covalently link small molecules of a combinatorial library to a substrate.

Combinatorial libraries constructed on polyester beads are necessarily bound covalently thereto at least during the construction reactions. For the determination of the molecular weight of a small molecule of such a library located at a particular address, i.e., at a particular site on a grid, it is necessary to break the covalent linkage in order to desorb intact molecules. For the purpose of testing requirements of an address-based determination, phenylalanine was adsorbed onto Sasrin® polystyrene beads and linked covalently thereon by means of reactive groups attached to the Sasrin® beads, using the methods of Mergler et al. I (*Tet. Lett.*, 29, 4005 (1988)) and Mergler et al. II (*Tet. Lett.*, 29, 4009 (1988)).

The formation of the covalent bond between phenylalanine and the Sasrin® bead dramatically reduced the yield of molecular ions in the SIMS spectrum. This effect is shown in FIG. 2B where the yield of $(M+H)^+$ at m/z 166 is no longer visible, although strong fragment ions are found at m/z 120. Accordingly, the parent compound, phenylalanine, could not be identified. When larger molecules were tested in otherwise identical experiments, parental molecular ions were not observed and the spectra were found to consist mainly of intense fragment ions from protecting groups and monomers, such as amino acids. For example, with the pentapeptide, leucine-serine-arginine-isoleucine-valine, the expected parental molecular ion at 587 m/z was not observed nor were any of the cationized species, although several fragment ions typical of each of the monomer units were found in the low mass range. See Mantus et al., *Anal. Chem.*, 65, 1431 (1993). Hence, the TOF-SIMS analysis of small molecules covalently bound to polyester beads was determined to be ineffective unless the covalent bond is broken prior to the TOF-SIMS analysis.

A protocol for clipping the covalent bond or bonds that bind a small molecule of a library to a suitable substrate, while leaving the small molecule resting in place on the substrate, was developed using phenylalanine attached to a Sasrin® polystyrene bead to test the protocol. Beads with covalently attached amino acids were then transferred to a copper grid. The copper grid was used as a support and markings on the grid were used to locate specific beads, i.e., addresses.

It was discovered that Sasrin® polystyrene beads form acid sensitive covalent bonds with peptides, for example. The beads having small molecules covalently attached thereto were placed in a chamber saturated with trifluoracetic acid (TFA) and methylene chloride ($CH_2Cl_2$) vapors from a 2% TFA in $CH_2Cl_2$ solution. A three minute exposure was sufficient to cleave the amino acid from the bead. The progress of the reaction was monitored by observing a color change from off-white to purple on the beads themselves. Once the cleavage reaction was complete, the beads and copper grid were inserted directly into the TOF-SIMS instrument for analysis.

Figure 4A:
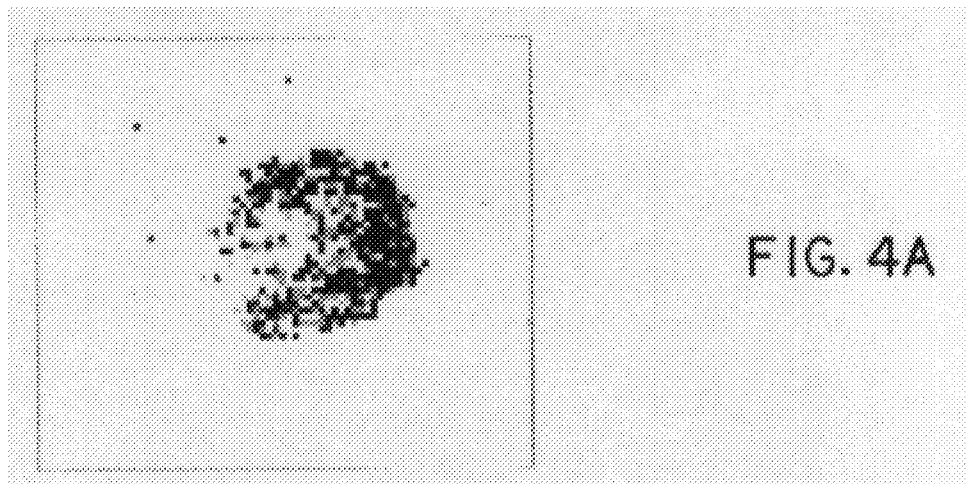
FIGS. 4(A) and 4(B) are a composite of two TOF-SIMS images, each directed at the same address on a copper grid.
Figure 4B:
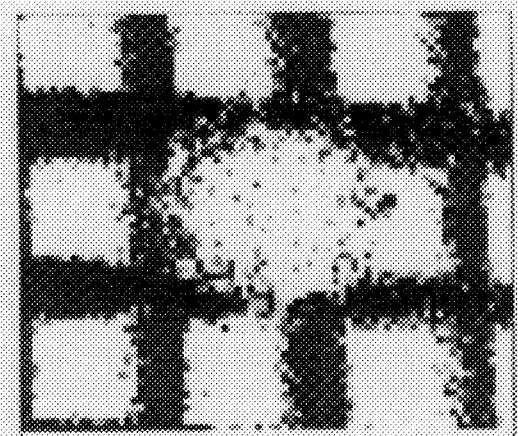

The mass spectra of the beads subjected to the vapor phase clipping exhibited a strong signal for each corresponding parent ion. The SIMS spectrum of the clipped phenylalanine is shown in FIG. 2C, while the corresponding image of m/z 166 is shown in FIG. 4. An important observation derived from FIGS. 4A and 4B, which are TOF-SIMS images directed at the identical address, but using different filters, is that the peptide is confined to the bead. This is evident because its signal (shown in FIG. 4A) is not found from the surrounding copper grid (shown in FIG. 4B). Therefore, the phenylalanine after breaking its covalent linkage to the polyester bead remained associated with the bead, due to physical adsorption or other weak molecular effects. Moreover, the signals observed for phenylalanine at m/z-(M+H)$^+$ in FIG. 2C are more intense than the same signal for phenylalanine when compared to the signals when it was simply physically adsorbed to a bead (FIG. 2A), perhaps due to the better uniformity of coverage on the bead resulting from the covalent bond formation. Therefore, greater sensitivity results from analyzing molecular species clipped from the beads than from analyzing those prepared by other methods, such as by physisorption alone.

Figure 5A:
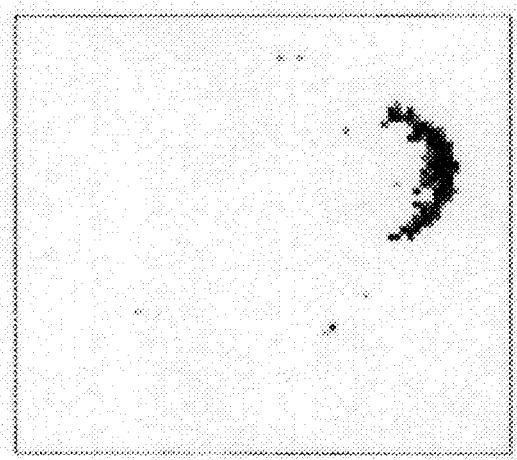
FIGS. 5(A) and 5(B) are a composite of two TOF-SIMS images, each directed at the same address on a copper grid.
Figure 5B:
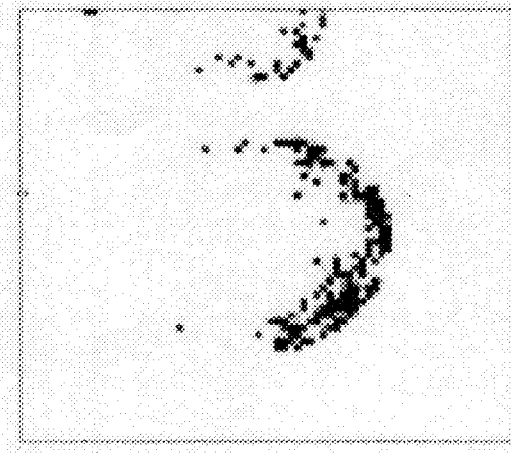
Figure 7A:
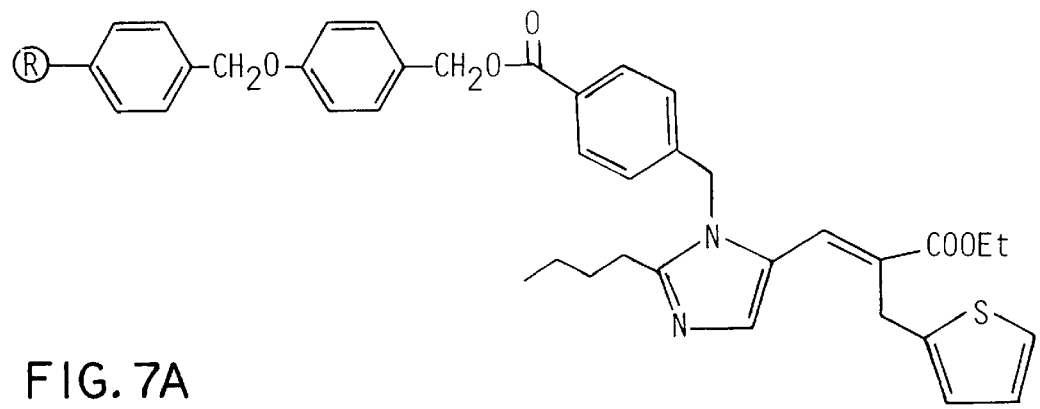
FIGS. 7(A)–7(E) depict the linking moieties attaching the angiotensin II receptor antagonist to various polystyrene beads.
Figure 7B:
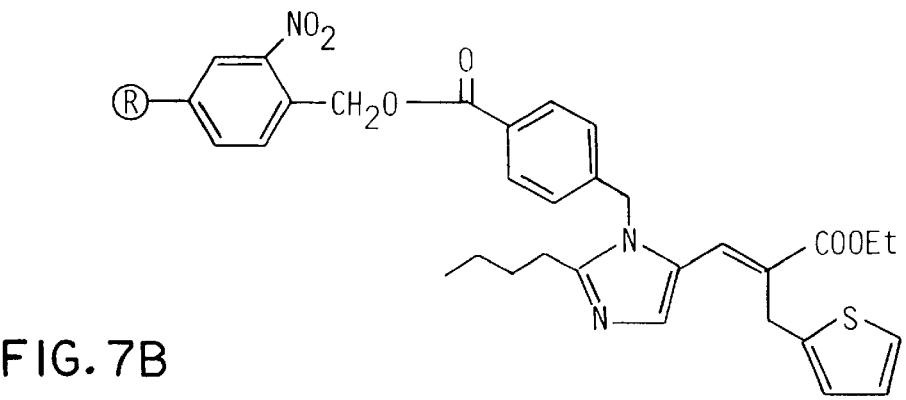
Figure 7C:
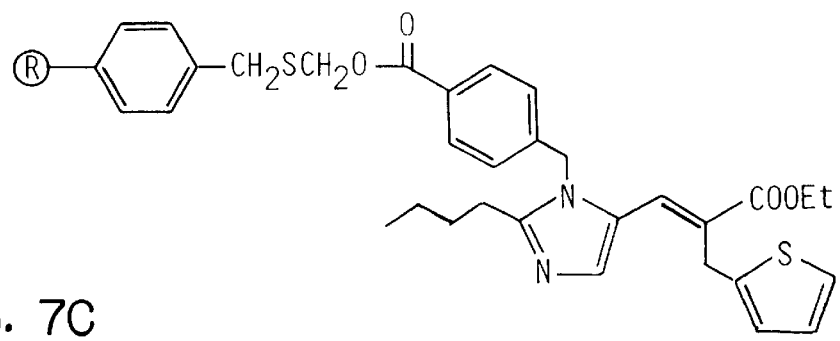
Figure 7D:
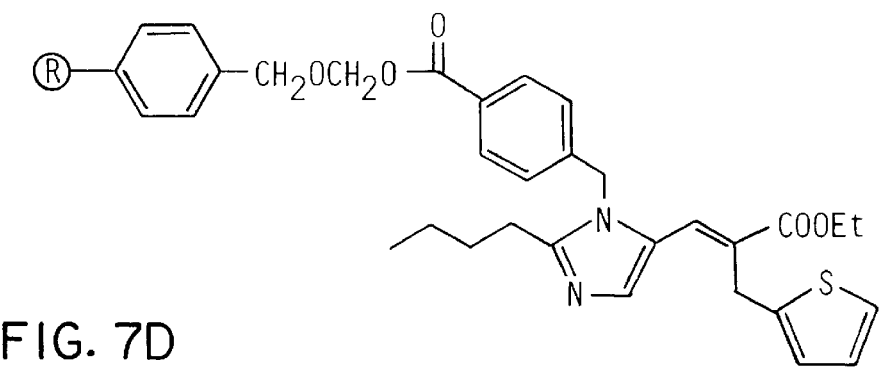
Figure 7E:
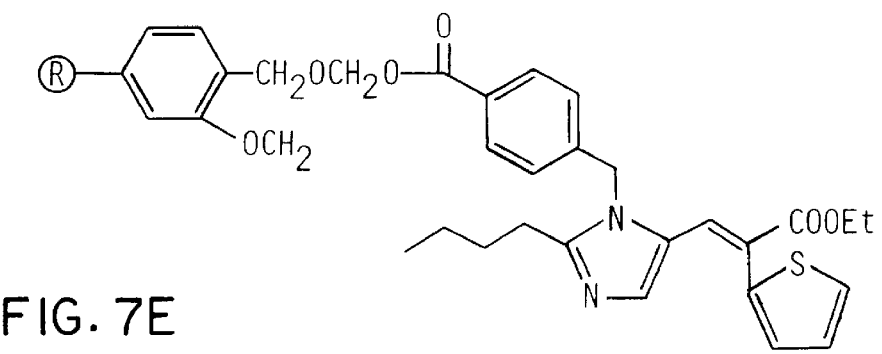

The technique was further tested by imaging a mixture of phenylalanine and leucine coated beads, using the same procedure as above. The beads were placed on a copper grid and cleaved with TFA as described above. The image is shown in FIG. 5, which is a field of view of 120 microns. Even though the beads were very close to each other there was no significant cross contamination, as seen by comparing FIG. 5A with FIG. 5B, wherein the (M+H)$^+$ ion intensity for leucine is shown in FIG. 5A and the (M+H)$^+$ ion intensity for phenylalanine is shown in FIG. 5B. As in FIG. 4, the images depicted in FIG. 5 are at the identical address, using different filters.

This example illustrates a method for further increasing the sensitivity of the TOF-SIMS molecular weight assay and, more significantly, illustrating a method for the determination of the molecular species contained in a library found at particular locations on a grid of beads containing different molecular species.

EXAMPLE 5

This example illustrates the TOF-SIMS assay as applied to the identification of a tripeptide covalently bound to a bead.

The tripeptide Val-Tyr-Val was covalently attached through an acid sensitive linker to the bead, according to the method described in Example 4. The bead was subjected to clipping by the vapor phase method and subjected to characterization by TOF-SIMS, as described in Example 2. The mass spectrum displayed in FIG. 6 (lower panel) shows ions at m/z 380 (M+H), 281, and 263. The assignment of these peaks is shown in the figure, which are the whole tripeptide, a Val-Tyr dipeptide fragment, and a Tyr-Val dipeptide fragment, respectively. In the low mass range (FIG. 6, upper panel), intense peaks were found at m/z 72 (Val-Co$_2$H) and 136 (Tyr-Co$_2$—H). Using the method of Biemann et al., Mass Spectrom. Rev., 6, 1 (1987), analysis of the TOF-SIMS spectrum of fragment sequence ions provided not only the composition, but the Val-Tyr-Val sequence through the above fragmentation pattern.

Accordingly, this method provided a determination of the mass of the parent ion and thereby demonstrates a method to identify directly those members of a library with a given molecular weight, as illustrated herein.

EXAMPLE 6

This example illustrates the use of the electrospray mass spectrometry to the identification of a heterocyclic small molecule covalently bound to the Sasrin® bead for comparison to the instant invention. The data disclosed in this example and Example 7 were provided by S. A. Carr, M. E. Hemling, G. D. Roberts, and J. Weinstock of the Chemical and Biological Research Division of SmithKline Beecham Pharmaceuticals, King of Prussia, Pa.

A bead having attached thereto angiotensin II receptor antagonist (ethyl 2-(2'-thiophenylmethyl)-3-[5'-{(1'-p-carboxyphenylmethyl)-2'-n-butyl}-imidazolyl]-propenoate) was isolated and transferred to a micro-Eppendorf tube. The analyte was permitted to cleave for 15 min with 1% TFA in methylene chloride. The sample was dried, and the compound was extracted/dissolved in 10 μl acetonitrile. One-tenth of the solution was introduced by flow injection and analyzed by ESMS on a Perkin Elmer Sciex API-III triple quadrupole analyzer (Thornhill, Ontario). An intense signal corresponding to the (M+H)+ ion was readily detected at m/z 453.18 (theor. 453.18), as set forth in FIG. 8A. Strong signals from the bead and the linker were also observed in the range m/z 500 to 600. An additional 10% of the solution was then analyzed by tandem MS on the same quadrupole instrument and the result is set forth in FIG. 8B. The molecular ion cluster was selected by Q1 of the triple quadrupole and collisionally activated with the argon in the collision cell, Q2. The product ions were detected in Q3. A large number of fragment ions were observed, all of which were readily assigned to the structure of the angiotensin II receptor antagonist.

Thus, electrospray mass spectrometry could be used to determine the molecular weight of covalently bound heterocyclic compound.

EXAMPLE 7

This example illustrates the identification of the angiotensin II receptor antagonist covalently bound to the Sasrin® bead by using the MALDI method, presented here for comparative purposes.

Figure 9A:
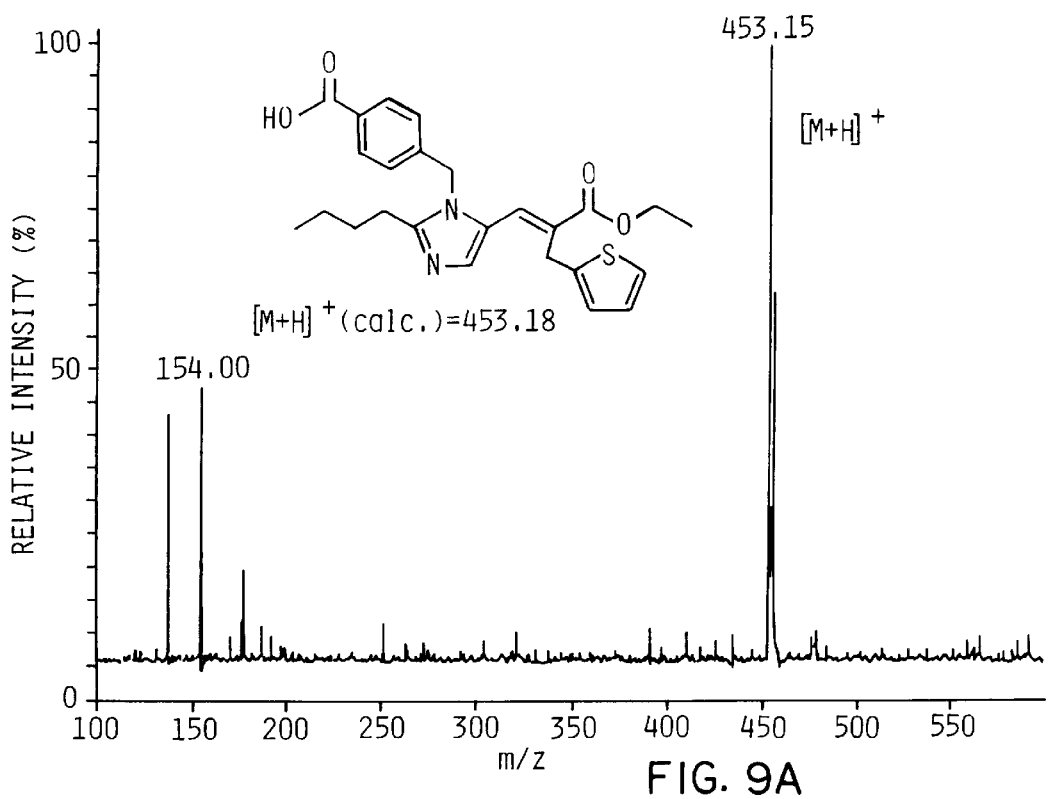
FIGS. 9(A) and 9(B) are the composite of matrix assisted laser desorption (MALDI) spectra of angiotensin II receptor antagonist. This data was provided for comparison with the present invention by S. A. Carr, M. E. Hemling, G. D. Roberts, and J. Weinstock of the Chemical and Biological Research Division of SmithKline Beecham Pharmaceuticals, King of Prussia, Pa.

The Sasrin® bead was placed on a stainless steel sample target and exposed for about 1 hr to TFA vapor in an enclosed chamber. A 0.5 μl alignment of a solution of dihydroxybenzoic (DHB) acid matrix in acetone was placed on the bead, and allowed to dry in air. Analyses were carried out using two types of Fisons VG MALDI mass spectrometers (Manchester, UK), both single-stage reflectron instruments using photon irradiation from a 337-nm pulsed nitrogen laser and 23-keV accelerating voltage. For generating conventional MALDI spectra, a low performance TOFSpec with maximum mass resolution in the reflecting mode of M/Δn 1200 (FWHM) was used. A conventional MALDI mass spectrum was generated by 41 laser shots that were averaged to produce the spectrum set forth in FIG. 9A. The instrument was mass calibrated externally using the (M+H)+ peaks of DHB and gramicidin S. A significant signal is observed for the (M+H)+ at m/z 453.15 (theor. 453.18). Fragments were not detected. Peaks below m/z 200 are primarily due to the DHB matrix. DHB has been found to be particularly useful for low M$_r$ organic compounds because it gives a very low matrix background above m/z 200.

Figure 9B:
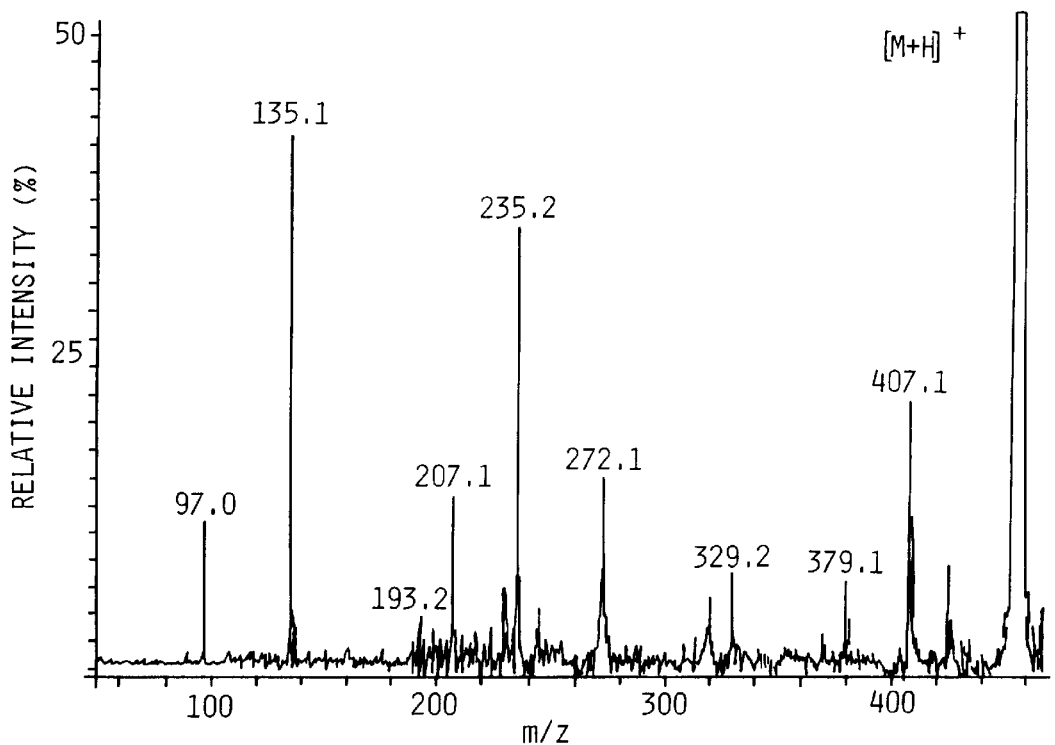

To overcome the fact that MALDI did not produce a significant fragment spectrum for this compound, the post source decay (PSD) method (see e.g., Della-Negra et al., Anal. Chem., 57, 2035 (1985); Tang et al., Anal. Chem., 60, 1791 (1988); Spengler et al., J. Phys. Chem., 96, 9678 (1992); Kaufmann et al., J. Mass Spectrom., 131, 355 (1994)) was applied to the angiotensin II receptor antagonist analysis using a VG TofSpec-SE instrument. An approximately 10 Da window centered on the parent ion at m/z 453.2 was selected for product ion analysis using a Bradbury-Nielson ion gate. PSD mass spectra were acquired in seven consecutive, overlapping mass scale segments, each representing a ca. 30% mass change from the previous segment. The PSD segments were combined and externally mass calibrated against a PSD spectrum of renin substrate tetradecapeptide by the data system to yield FIG. 9B. The spectrum was readily interpreted using well-developed rules for the interpretation of fragment ions.

Thus Example 7 illustrates that the covalently bound heterocyclic compound can be clipped by TFA and its molecular weight determined by MALDI.

obtained by bombarding with $2.2 \times 10^7$ $Ga^+$ ions. Assuming $10^{14}$ molecules $cm^{-2}$, less than 0.5% of the surface has experienced an ion impact. This is well within the static limit for SIMS. The (M+H)+ at m/z 453 is clearly evident together with the significant fragment peaks at m/z 283, 135 and 97. The internal calibration procedure using the H+ and the $CH_3$+ ions yield a m/z for the (M+H)+ ion of 453.18 (theor. 453.18). The accuracy of the calibration was checked by incorporating a CsI internal standard and using the Cs+ at m/z 133. The fragment masses in FIG. 10 can be determined with similar accuracy, which also aids both in their assignment and in their use along with the molecular mass in defining the identity of the target compound.

The calculated and observed masses of fragment ions of the angiotensin II receptor antagonist detected in the illustrative examples 6–8 are set forth in Table 1 below. It is clear that the errors in the masses are negligible and that the three mass spectrometric techniques described above are suitable for identifying polymer bound small molecules that may be present at picomole quantities. The TOF-SIMS method has even greater sensitivity than MALDI as shown by the smaller magnitude of the error in the experimental masses.

TABLE 1

Figure 10C:
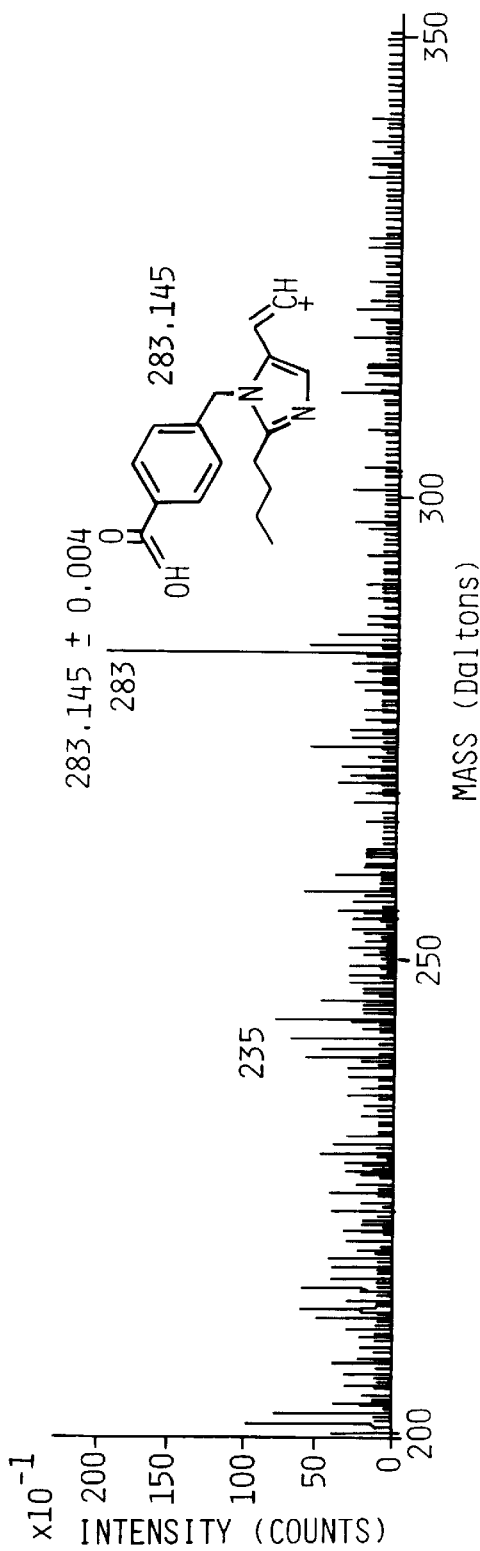

Calculated and observed masses of fragment ions in FIGS. 8B, 9, and 10A

| | | Experimental masses (errors) | | |
|---|---|---|---|---|
| Composition | Calc. Mass | ESMS[b] | MALDI[b] | TOF-SIMS |
| $C_5H_5S$ | 97.0112 | 96.96 (0.05) | 97.0 (0.0) | 97.015 (0.004) |
| $C_8H_7O_2$ | 135.0446 | 134.99 (0.05) | 135.1 (0.1) | 135.045 (0.000) |
| $C_{11}H_{15}N_2O_2$ | 207.1133 | 207.02 (0.09) | 207.1 (0.0) | not obsd. |
| $C_{11}H_{19}N_2O_2$ | 235.1447 | 235.07 (0.07) | 235.2 (0.1) | not obsd. |
| $C_{15}H_{16}N_2O_1S$ | 272.0983 | 272.06 (0.04) | 272.1 (0.0) | not obsd. |
| $C_{17}H_{19}N_2O_2$ | 283.1446 | not obsd. | not obsd. | 283.144 (0.001) |
| $C_{19}H_{21}N_2O_4$ | 341.1501 | 341.17 (0.02) | v. weak | not obsd. |
| $C_{21}H_{25}N_2O_4$ | 369.1814 | 369.22 (0.04) | weak | not obsd. |
| $C_{23}H_{23}N_2O_3S$ | 407.1429 | 407.21 (0.07) | 407.1 (0.1) | not obsd. |
| $C_{23}H_{25}N_2O_4S$ | 425.1535 | 425.22 (0.07) | 425.0 (not measured) | not obsd. |
| $C_{25}H_{29}N_2O_4S$ | 453.1848 | 453.18 (0.00)[a] | 453.15 (0.03)[a] | 453.183 (0.002) |

[a]Values were obtained from normal spectra, not MS/MS or PSD spectrum.
[b]ESMS and MALDI data were provided by S. A. Carr, M. E. Hemling, G. D. Roberts, and J. Weinstock of the Chemical and Biological Research Division of SmithKline Beecham Pharmaceuticals, King of Prussia, Pennsylvania.

EXAMPLE 8

This example illustrates the identification of the angiotensin II receptor antagonist bound to the Sasrin bead by the TOF-SIMS method.

TOF-SIMS studies of the beads were carried out after exposure to the beads of TFA vapor for a period of 2 hours in an enclosed chamber. The beads were supported on a small piece of silicon wafer. After the TFA vapor treatment, the wafer was transferred directly into the SIMS analysis chamber of a Kratos Prism TOF-SIMS instrument, and the analysis was carried out. A pulsed 25-keV primary ion beam (minimum beam diameter 200 nm) irradiated the sample; the pulse width was 7 ns. A 2.5-keV stage voltage was used to accelerate the ions into the analyzer, which is a reflectron device capable of mass resolution better than m/Δm=10,000. The analytical data were output as either mass spectra or mass-resolved images.

Figure 10D:
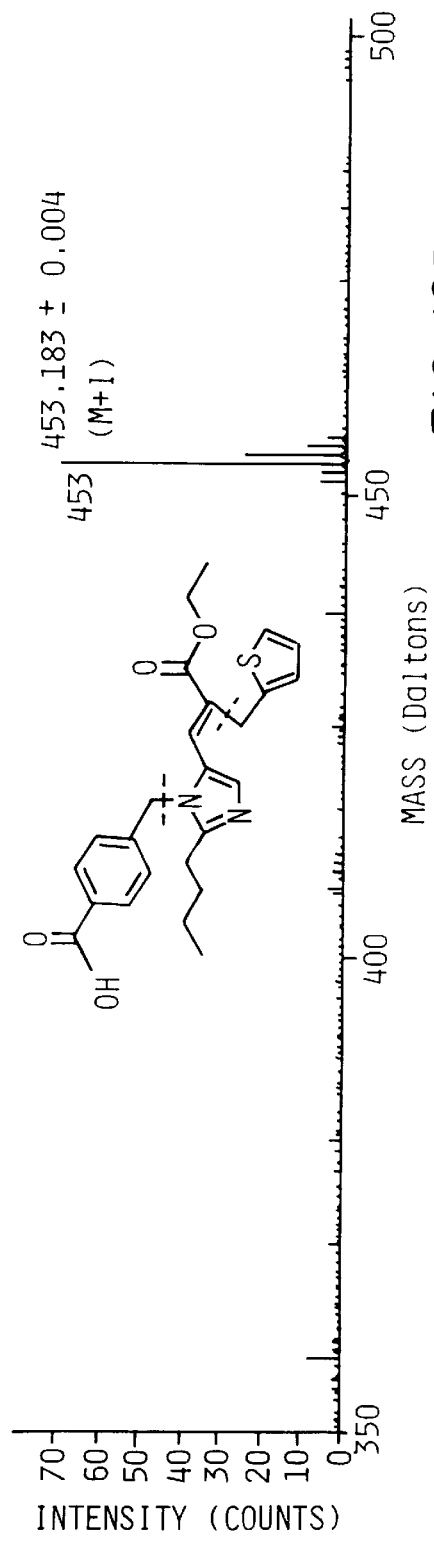
Figure 11A:
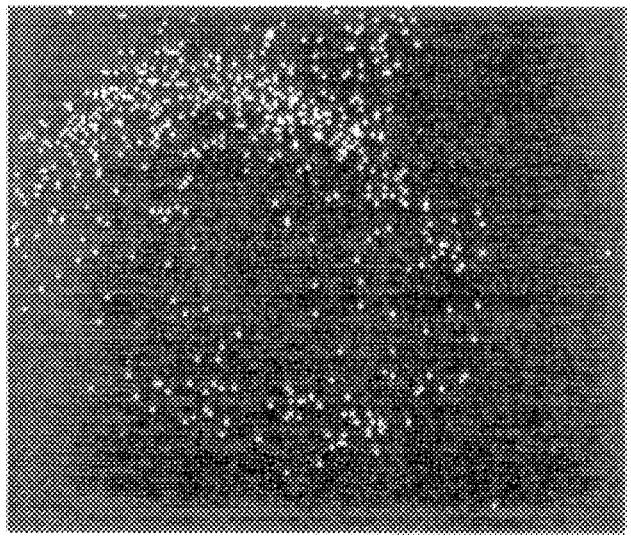
FIGS. 11(A) and 11(B) are the composite of two images of the angiotensin II receptor antagonist.
Figure 11B:
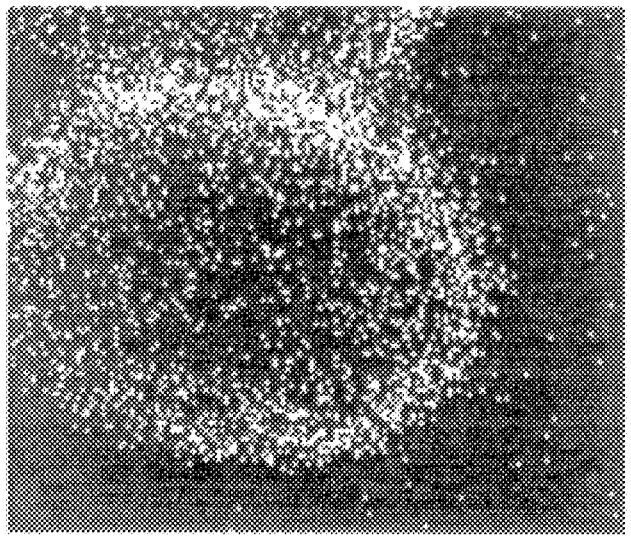

FIG. 10 sets forth the positive ion spectrum obtained from a single bead with a diameter of about 50 μm that had been FIG. 11 sets forth two images obtained by collecting secondary ions as the primary beam is rastored across the bead surface. The images show the ion collection distribution for (A) the (M+H)+ ion and (B) the m/z 135 ion. It is clear that the ions attributable to the target compound are collected primarily from the bead and few ions are evident from the silicon support. Thus, the images demonstrate that even after the TFA treatment, the target compound remains substantially on the bead.

Thus, Example 8 illustrates that a heterocyclic compound covalently bound to a substrate can be clipped by TFA and its molecular weight determined by TOF-SIMS.

EXAMPLE 9

This example sets forth the results of a TOF-SIMS assay of the present invention directed to the aforementioned angiotensin II receptor antagonist covalently attached to the Wang resin, the Acetal resin, or the Thioacetal resin.

Angiotensin II receptor antagonist-substrate constructs were constructed using the Wang resin, the Acetal resin, or the Thioacetal resin as substrate. The antagonist-substrate covalent linkage was effected using linkers associated with the respective linkers, as shown in FIG. 7. The covalent linkages were clipped by exposure to TFA vapor. TOF-SIMS was applied to each of the above resin samples and the molecular weight of the antagonist was determined successfully.

The contents of each of the references identified herein are hereby incorporated by reference in their entirety.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of obtaining a molecular weight of individual small molecules of a combinatorial library comprising:
   (a) forming a plurality of complexes of solid substrates and said small molecules, each of said complexes comprising one substrate, or portion thereof, and at least one of said small molecules of said combinatorial library, wherein said substrate and said small molecule are attached to one another by a covalent bond;
   (b) breaking said covalent bond such that said small molecule remains physically adsorbed to said substrate; and
   (c) determining the molecular weight by secondary ion mass spectrometry of said small molecule adsorbed to said substrate.

2. The method of claim 1, wherein said small molecules are selected from the group consisting of amino acids, peptides, oligonucleotides, heterocyclic compounds, and combinations thereof.

3. The method of claim 2, wherein said substrate comprises a polymeric resin having a linking moiety attached thereto.

4. The method of claim 3, wherein said polymeric resin is a polystyrene resin having a linking moiety attached thereto.

5. The method of claim 4, wherein said linking moiety comprises at least one reactive group that is selected from the group consisting of hydroxyl, amino, carboxyl, acetal, thioacetal, $C_1$–$C_{10}$ alkylamino, $C_1$–$C_{10}$ aralkylamino, and $C_1$–$C_{10}$ haloalkyl, and an o-nitrobenzylic group having a benzylic hydrogen.

6. The method of claim 5, wherein said linking moiety is selected from the group consisting of F-moc-2,4-dimethoxy-4'-(carboxymethyloxy)-benzhydrylamine, F-moc-methoxy-4'-(gamma-carboxypropyloxy)benzhydrylamine, p-alkoxybenzyl alcohol, benzylacetal, benzylthioacetal, benzhydrylamine, Cl—CH$_2$-Ph, 2-methoxy-4-alkoxy benzyl alcohol, and o-nitrobenzyloxy carbonyl.

7. The method of claim 6, wherein said linking moiety is selected from the group consisting of 2-methoxy-4-alkoxy benzyl alcohol, benzylacetal, and benzylthioacetal.

8. The method of claim 7, wherein said covalent bond is broken without substantial modification of said small molecule.

9. The method of claim 8, wherein said covalent bond is broken by using a vapor comprising trifluoracetic acid.

10. The method of claim 9, wherein said covalent bond is broken by using a mixture of trifluoracetic acid and methylene chloride vapors.

11. The method of claim 10, wherein said substrate is a bead.

12. The method of claim 11, wherein said bead has a diameter of from about 10 microns to about 120 microns.

13. The method of claim 11, wherein said secondary ion mass spectrometry is time-of-flight secondary ion mass spectrometry.

14. The method of claim 13, wherein said method further comprises mapping of the spatial distribution of said small molecules on said beads.

15. The method of claim 12, wherein said small molecule is an amino acid or a peptide.

16. The method of claim 15, wherein said peptide comprises two to ten amino acids.

17. The method of claim 16, wherein said method further comprises determination of the sequence of said peptide from the fragmentation pattern obtained in said time-of-flight secondary ion mass spectrometry.

18. The method of claim 13, wherein said small molecule is a heterocyclic compound comprising four to seven membered rings having N, S, or O, and combinations thereof.

19. The method of claim 1, wherein said substrate is a polystyrene bead having a reactive group, said small molecule is an amino acid, peptide, oligonucleotide, or a heterocyclic compound, or a combination thereof, said covalent bond is an acid sensitive ester bond, said covalent bond is broken by exposing said complex placed on a grid to the vapors of trifluoracetic acid and methylene chloride, and said secondary ion mass spectrometry is time-of-flight secondary ion mass spectrometry.

* * * * *